United States Patent [19]
Eberlein et al.

[11] Patent Number: 5,550,214
[45] Date of Patent: Aug. 27, 1996

[54] ISOLATED ANTIGENIC ONCOGENE PEPTIDE FRAGMENTS AND USES

[75] Inventors: Timothy J. Eberlein, Dover; George E. Peoples, Newtonville; Ichiro Yoshino, Brookline; Peter Goedegebuure, Brighton, all of Mass.

[73] Assignee: Brigham and Women's Hospital, Boston, Mass.

[21] Appl. No.: 195,075

[22] Filed: Feb. 10, 1994

[51] Int. Cl.⁶ .............................. A61K 38/08; C07K 4/12
[52] U.S. Cl. .......................... 530/328; 530/300; 530/403; 514/2; 514/15; 930/230; 424/184.1; 424/185.1; 424/277.1; 424/155.1; 424/154.1; 424/174.1
[58] Field of Search ..................................... 530/328, 403, 530/300; 514/15, 2; 930/230; 424/184.1, 185.1, 277.1, 155.1, 154.1, 174.1

[56] References Cited

U.S. PATENT DOCUMENTS 4,968,603  11/1990  Slamon et al. ............................. 435/6

FOREIGN PATENT DOCUMENTS 9008160     7/1990  WIPO.
WO94/20127  9/1994  WIPO.

OTHER PUBLICATIONS

*Webster's II New Riverside University Dictionary*, Houghton Miflin Co., Boston, MA. p. 433.

Nijman et al., "Characterization of cytotoxic T Lymphocyte Epitopes of a self–protein, p53, and a non–self–protein, influenza matrix: relationship between major histocompatibility complex peptide binding affinity and immune responsiveness to peptides", Jour. of Immun., 14:121–126, 1993.

Parker et al., "Sequence motifs important for peptide binding to the human MHC class I molecule, HLA–A2", vol. 149, 3680–3587, No. 11, Dec. 1, 1992 (J. Immunol.).

Parker et al., "Scheme for ranking potential HLA–A2 binding peptides based on independent binding of individual peptide side–chains", The Journal of Immunology, vol. 152, No. 1, Jan. 1, 1994.

Peoples et al., "Breast and ovarian cancer–specific cytotoxic T lymphocytes recognize the same HER2/neu–derived peptide", Proc. Natl. Sci., vol. 92, pp. 432–436, Jan. 1995.

Sauma et al., "Recognition by HLA–A2–restricted cytotoxic T Lymphocytes of endogenously generated and exogenously provided synthetic peptide analogues of the influenza A virus matrix protein", Human Immunology, 37, pp. 252–258, 1993.

Yoshino et al., "HER2/neu–derived peptides are shared antigens among human non–small cell lung cancer and ovarian cancer", Cancer research, 54, 3387–3390, Jul. 1, 1994.

"Cytotoxic T Cells Isolated from Ovarian Malignant Ascites Recognize a Peptide Derived from the HER–2/neu Proto–oncogene" Constatin G. Ioannides et al. *Cellular Immunology*, 151, 225–234 (1993).

"CTL Clones Isolated From Ovarian Tumor Infiltrating Lymphocytes Can Recognize Peptides With Sequences Corresponding To The HER2/NEU Gene Product" Ionnides C. G. et al. *1992 FASEB Meeting* Apr. 2–9.

"T–cell Recognition Of Ovarian Cancer" George E. Peoples et al. *Surgery* 227–234 Aug. 1993.

"Allele–Specific Motifs Revealed By Sequencing Of Self––Peptides Eluted From MHC Molecules" Falk et al. *Nature* vol. 351 290–296 May 23, 1991.

"HLA–A2 Presents Shared Tumor–Associated Antigens Derived From Endogenous Proteins In Ovarian Cancer" George E. Peoples et al. *The Journal of Immunology* vol. 151, 5481–5491, No. 10 Nov. 15, 1993.

"Cytotoxic T–Cell Clones Isolated From Ovarian Tumour Infiltrating Lymphocytes Recognize Common Determinants on Non–Ovarian Tumour Clones" C. G. Ioannides et al. *Scand. J. Immunol.* 37, 413–424, 1993.

"Prominent Role of Secondary Anchor Residues In Peptide Binding To HLA–A2.1 Molecules" Jörg Ruppert et al. *Cell* vol. 71, 929–937, Sep. 10, 1993.

(List continued on next page.)

*Primary Examiner*—Christopher S. F. Low
*Attorney, Agent, or Firm*—Choate, Hall & Stewart

[57] ABSTRACT

An isolated antigenic peptide fragment that is an isolated oncogene protein fragment is disclosed. The isolated peptide fragment of the invention is a peptide either 9 or 10 amino acid residues in length that includes at least a leucine residue at the C- terminus (i.e., position 9 or position 10). The peptide fragment is capable of binding in an HLA-A2 binding cleft and is capable of stimulating proliferation of at least one tumor-specific cytotoxic T-lymphocyte. Preferred peptides further include an isoleucine residue at position 2 and a valine residue at position 6. The most preferred isolated peptides can stimulate proliferation of cytotoxic T-lymphocytes obtainable from peripheral blood lymphocytes, ovarian tumors, breast tumors, gastric tumors, non-small cell lung tumors, pancreatic tumors, colon tumors, gliomas, bladder tumors, endometrial tumors and neuroblastomas. The preferred isolated peptide of the invention is a mutant peptide defined by SEQ ID NO.:2 or its functional equivalents.

Isolated cytotoxic T-lymphocytes capable of recognizing isolated peptides of the invention, particularly the HER2/neu mutant peptide are disclosed. These lymphocytes are especially useful for killing tumors or other cells which present on their surfaces the antigenic peptides of the invention. In particular, the lymphocytes are obtainable from ovarian tumor cells, breast tumor cells and non-small-cell lung tumor cells.

A method of stimulating proliferation of tumor-specific cytotoxic T-lymphocytes is described. This method includes obtaining lymphocytes from tumor tissue and contacting the lymphocytes with a peptide of the invention under conditions sufficient for the cytotoxic T-lymphocytes to proliferate. Therapeutically effective compositions containing the HER2/neu peptides are also described.

2 Claims, 4 Drawing Sheets

OTHER PUBLICATIONS

"The Minimum Peptide Epitope From The Influenza Virus Matrix Protein" Maria A. Bednarek et al. *The Journal of Immunology* vol. 147, 4047–4053, No. 12, Dec. 15, 1991.

"Studies Of The HER-2/neu Proto-oncogene In Human Breast and Ovarian Cancer" Dennis J. Slamon er al. *Science,* vol. 244, 707–712, 1980.

"Tyrosine Kinase Receptor With Extensive Homology To EGF Receptor Shares Chromosomal Location With neu Oncogene" Lisa Coussens et al. *Science* vol. 230, 1132–1139, Dec. 6, 1985.

"Similarity Of Protein Encoded By The Human c–erb–B–2 Gene To Epidermal Growth Factor Receptor" Tadashi Yamamoto et al. *Nature* vol. 319, 230–234, Jan. 16, 1986.

"erbB–2 Is A Potent Oncogene When Overexpressed In NIH/3T3 Cells" Pier Paolo Di Fiore et al. *Science* vol. 237, 178–182, Jul. 10, 1987.

ISOLATED ANTIGENIC ONCOGENE PEPTIDE FRAGMENTS AND USES

The present invention was funded, in part by National Institute of Health Grants R01CA45484 and CA09535. The United States Government may have certain rights in the invention.

BACKGROUND OF THE INVENTION

The immune system plays a central role in the body's defense against cancer. Cellular immunity against tumors can be demonstrated in part because the ability of T-lymphocytes to engage in cell-mediated attack against tumor cells is made possible by the interaction between the T-lymphocyte receptor ("TCR": T-cell receptor) and specific class 1 HLA tumor cell markers (i.e., human leukocyte antigens: "HLA" molecules) present on the surface of the tumor cell. The TCRs on T-lymphocytes recognize a tumor antigen when the tumor antigen is associated with the HLA surface cell molecules. In particular, CD8 T-lymphocytes recognize antigens made within, or otherwise introduced into, the cytoplasm of the cell. Antigens in the cells are cleaved by cytoplasmic proteases into peptide fragments. The fragments are transported by an active transport process mediated by molecules encoded in the HLA itself into the endoplasmic reticulum where the fragments bind to newly made class I molecules. The peptide fragment is transported out to the cell surface where the T-lymphocytes recognize the combination of peptide and HLA. The peptide binds in the groove of the HLA molecule between two alpha helices that form the sides of the groove.

Through this recognition of presented surface tumor antigen (i.e., tumor-associated antigen: "TAA"), the T-lymphocytes are activated, expanded by clonal selection, and matured to give rise to tumor-specific, cytotoxic T-effector cells ("cytotoxic T-lymphocytes") together with an enlarged population of T-memory cells. Unfortunately, tumor cells are not especially effective in mediating strong immune responses.

The identity of the TAA's themselves is generally unknown. Recently, TAA's have been investigated in two different tumor systems. It has been demonstrated that T-lymphocytes recognize specific TAA presented by HLA moieties on the surface of melanoma cells; the so-called MAGE system. See for example, Kawakami et al., J. Immunol., 148:638, (1992). The MAGE system is, however, expressed in only 40-50% of these tumors which make up only about 1 percent of all cancers. The MZ2-E antigenic peptide of the MAGE system is presented by HLA-A1 molecules which are found in only 26% of Caucasians. Specific recognition of ovarian cancer TAA by T-lymphocytes has also been demonstrated. See Ioannides et al., Cell Immunol. 151:225-234(1993), incorporated herein by reference.

A source of the ovarian cancer TAA may be fragments of oncogene protein products. HER2/neu (also called c-erbB-2) is a 185 kDa transmembrane glycoprotein with tyrosine kinase activity and extensive homology to epidermal growth factor. HER2/neu is a ubiquitous oncogene which is expressed in normal cells (Coussens et al., Science, 230:1132) and overexpressed in about 30% of all ovarian and breast cancers. Overexpression of the HER2/neu oncogene correlates with a poor prognosis in these cancers. See Slamon et al., U.S. Pat. No. 4,968,603 (Nov. 6, 1990), incorporated herein by reference.

The identity of specific antigenic peptide fragments which are the target of T-lymphocyte recognition would allow peptides to be used to stimulate T-lymphocytes in vitro for specific adoptive immunotherapy.

Nonetheless, although HER2/neu is widely expressed in epithelial tumors such as ovarian, breast, lung, gastric, pancreatic, and colon (see, for example, Yamanaka et al., Human Pathology, 24:1127-1134(1993); Kern et al., Am. J. Resp. Cell Mol. Biol. 9:448-454(1993)), only peptide fragments based on HER2/neu proteins from normal cells have heretofore been shown to provide recognition for cytotoxic T-lymphocytes. See Ioannides et al., Abstract FASEB Meeting, 1992 page A1404. Furthermore, because of their amino acid sequence and size, these "normal" HER2/neu peptide fragments are not actually predicted to bind with HLA-A2 molecules on the tumor surface.

This is unfortunate because vaccines and immunotherapies based upon antigenic HER2/neu peptides ideally should be tumor-specific so that cytotoxic T-lymphocytes (CTL's) will consistently attack only the tumor, not normal tissue. Thus, truly useful antigenic peptides should be capable of initiating immune responses against tumor cells only.

SUMMARY OF THE INVENTION

The present invention pertains to an isolated antigenic peptide fragment from tumor cells that is an isolated oncogene protein fragment.

An isolated peptide fragment of the invention is a peptide of either 9 or 10 amino acid residues in length that includes at least a leucine residue at the C-terminus (i.e., position 9 or position 10). The peptide fragment is capable of binding in an HLA-A2 binding cleft and is capable of stimulating proliferation of at least one cytotoxic T-lymphocyte. Preferred peptides further include an isoleucine residue at position 2 and a valine residue at position 6. The most preferred isolated peptides can stimulate proliferation of cytotoxic T-lymphocytes obtainable from peripheral blood lymphocytes, ovarian tumors, breast tumors, gastric tumors, non-small cell lung tumors, pancreatic tumors, colon tumors, gliomas, bladder tumors, endometrial tumors and neuroblastomas.

In a preferred embodiment, the antigenic peptides are derived from a portion of the mutant HER2/neu protein found in tumor cells and not found in normal cells. This preferred isolated peptide of the invention is a mutant peptide with an amino acid sequence defined by SEQ ID NO.:2 or its functional equivalents.

An isolated nucleic acid sequence of the invention is a nucleic acid sequence capable of encoding a peptide fragment of either 9 or 10 amino acid residues in length, the peptide fragment including at least a leucine residue at a C-terminus and capable of engaging with an HLA-A2 binding cleft. The encoded peptide is also capable of stimulating proliferation of at least one cytotoxic T-lymphocyte when the peptide is bound in an HLA-A2 binding cleft. Preferred nucleic acid sequences are capable of encoding a mutant HER2/neu peptide fragment (e.g., SEQ ID NO.:2) that is of sufficient size and amino acid composition to engage with an HLA-A2 binding cleft.

Another aspect of the invention is a recombinant vector including the isolated nucleic acid of the invention. Another embodiment of the invention is a host cell containing the recombinant vector.

A further embodiment of the invention provides isolated cytotoxic T-lymphocytes capable of recognizing isolated peptides of the invention, particularly the HER2/neu mutant peptide, when the peptide is engaged with an HLA-A2 binding cleft. These lymphocytes are especially useful for killing tumors or other cells which present on their surfaces the antigenic peptides of the invention. In particular, the lymphocytes are obtainable from peripheral blood lymphocytes, ovarian tumor cells, breast tumor cells, non-small cell lung tumor cells, pancreatic tumors, colon tumors, gliomas, bladder tumors, endometrial tumors, neuroblastomas and gastric tumors.

The invention further encompasses a method of stimulating proliferation of tumor-specific cytotoxic T-lymphocytes. This method includes obtaining T-lymphocytes from tumor tissue and contacting the lymphocytes with a peptide of the invention under conditions sufficient for cytotoxic T-lymphocytes to proliferate. Preferably, T-lymphocytes are contacted with a mutant HER2/neu peptide under conditions wherein it is engaged with an HLA-A2 binding cleft. The proliferated tumor-specific cytotoxic T-lymphocytes are separated.

A composition is also described. A preferred composition includes as one of its components an isolated HER2/neu mutant peptide of sufficient size and amino acid composition to engage with an HLA-A2 presentation moiety binding cleft. The composition may also include an antigen-presenting cell, such as a T2 cell, in combination with the antigenic peptide. This particular composition is especially useful in in vitro proliferation of tumor-specific CTL's.

It is an object of the present invention to provide an antigenic peptide capable of binding with the HLA-A2 binding cleft.

It is a further object of the present invention to provide an antigenic peptide capable of binding with the HLA-A2 binding cleft that stimulates proliferation of cancer-specific CTL's and induces cytoxicity and/or cytokine release.

It is another object of the invention to provide a means for stimulating proliferation of cytotoxic T-lymphocytes useful for killing tumors (i.e., ovarian tumors, breast tumors, gastric tumors, non-small cell lung tumors, pancreatic tumors, colon tumors, gliomas, bladder tumors, endometrial tumors and neuroblastomas) or other cells which present on their surfaces the antigenic peptides of the invention.

DETAILED DESCRIPTION OF THE DRAWINGS

Figure 5:
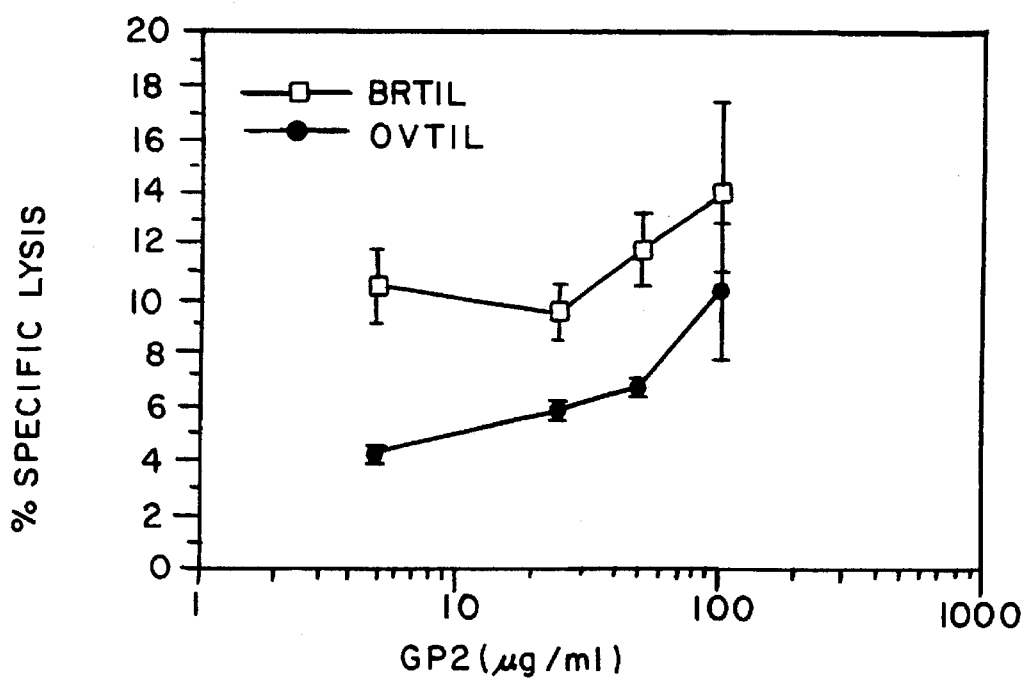

FIG. 5 illustrates that OvTIL recognizes SEQ ID NO.:2 in a dose response manner. OvTIL were tested in chromium release assays against T2 pulsed with increasing levels of SEQ ID NO.:2 ("GP2"). Incubations were for 1 hour at an E:T of 20:1 and peak recognition occurred at 100 ug/ml.

Figure 6:
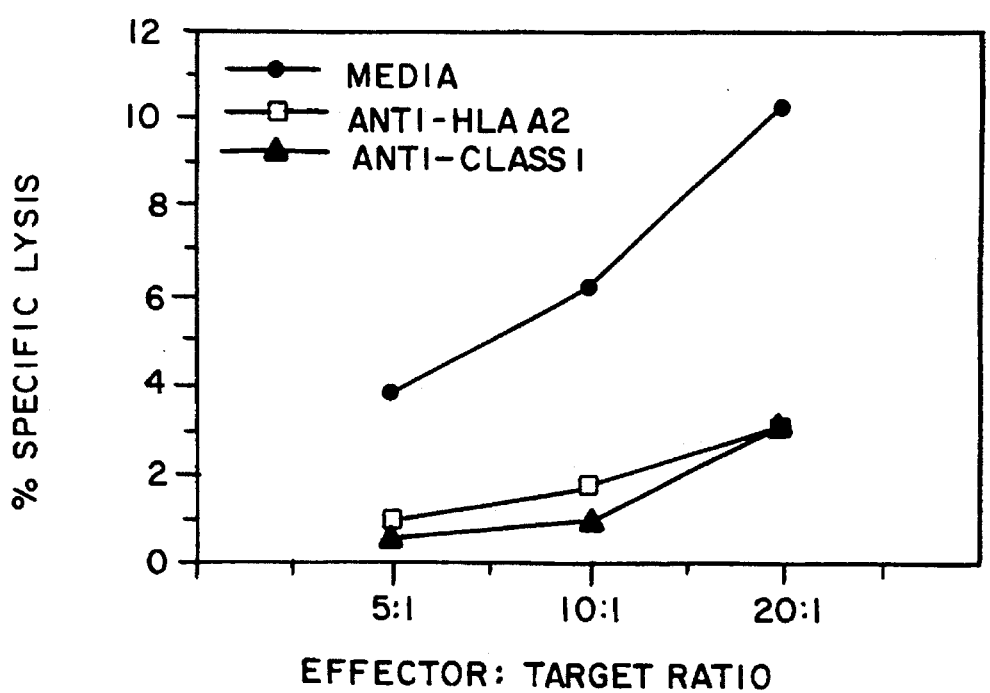

FIG. 6 illustrates that recognition of SEQ ID NO.:2 ("GP2") is HLA-A2 restricted. T2 was chromium labelled, pulsed with SEQ ID NO.:2, and pulsed with monoclonal antibodies added at 1:2 dilution of hybridoma supernatant for 30 minutes at 37 degrees C prior to chromium release assays. The data presented is for OvTIL1 and is representative of multiple assays performed.

Figure 7:
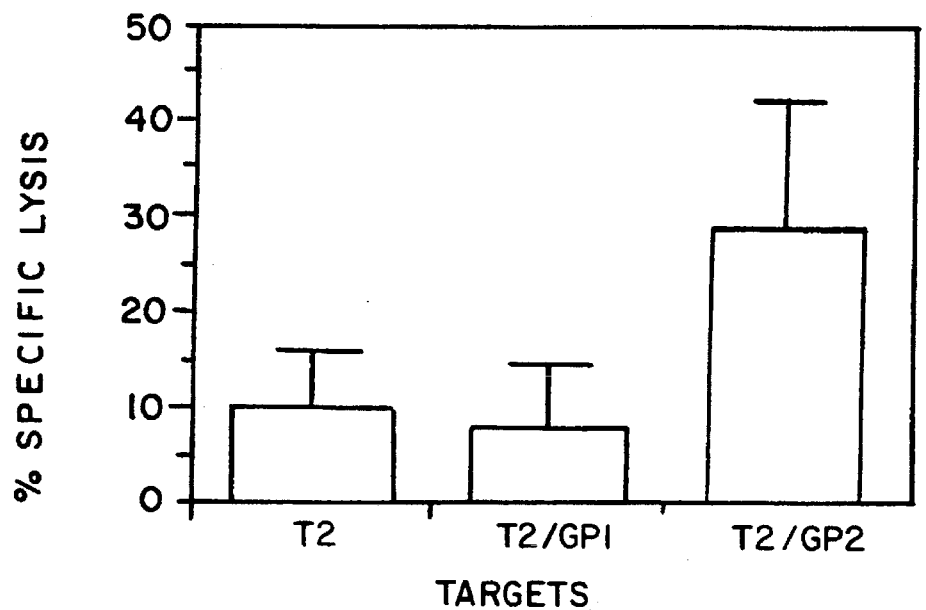

FIG. 7 illustrates results of chromium release assays that demonstrate non small-cell lung cancer-specific CTL's recognize the HER2/neu-derived peptide (SEQ ID NO.:2). TIL's were tested against T2 either unloaded or pulsed with 50–100 ug of SEQ ID NO.1 or 2 at an E:T ratio of 20:1.

Figure 8:
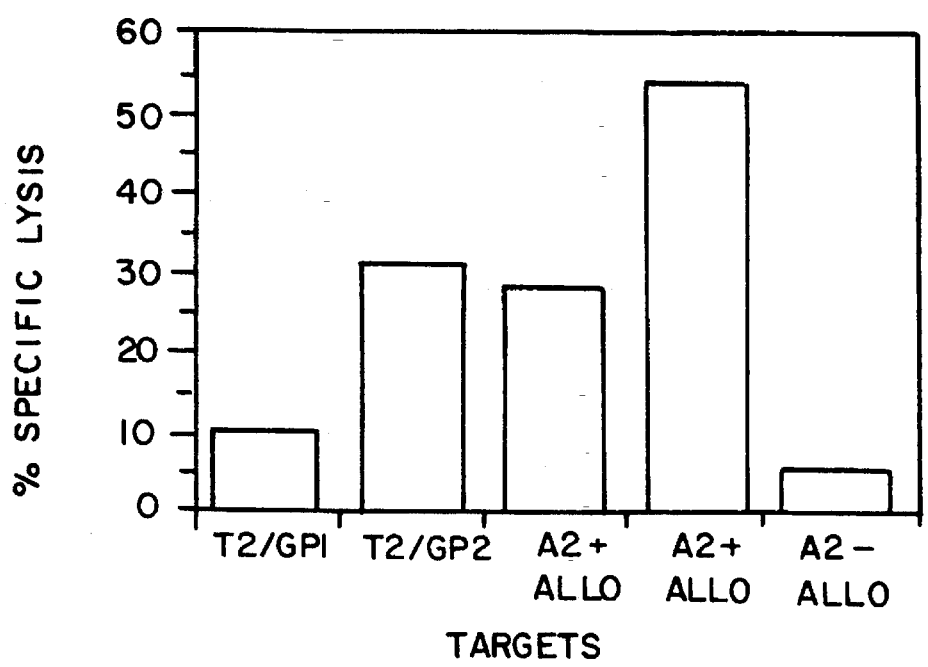

FIG. 8 illustrates results of chromium release assays that demonstrate ovarian cancer T-lymphocytes that have been educated with SEQ ID NO.:2 recognize HLA-A2$^+$, HER2/neu$^+$ allogenic tumors. T-lymphocytes were tested against T2 targets loaded with 50–100 ug of SEQ ID NO.1 (bar 1) or SEQ ID NO.:2 (bar 2), A2 positive ovarian tumor targets (bars 3 and 4), and an A2 negative ovarian tumor target (bar 5), all at an E:T ratio of 20:1.

DESCRIPTION OF THE SEQUENCES

SEQ ID NO.:1 is the wild-type HER2/neu peptide fragment (Ile Leu Ser Ala Val Val Gly Ile Leu);

SEQ ID NO.:2 is a mutant HER2/neu peptide fragment (Ile Ile Ser Ala Val Val Gly Ile Leu);

SEQ ID NO.:3 is the canonical HER2/neu sequence containing anchor binding residues to the HLA-A2 cleft (Xaa Ile Xaa Xaa Xaa Val Xaa Xaa Leu);

SEQ ID NO.:4 is HER2/neu peptide that does not induce proliferation of cancer-specific CTL's (Pro Leu Thr Ser Ile Ile Ser Ala Val);

SEQ ID NO.:5 is a functional variant of SEQ ID NO.:2 (Tyr Ile Ser Ala Val Val Gly Ile Leu);

SEQ ID NO.:6 is a functional variant of SEQ ID NO.:2 (Phe Ile Ser Ala Val Val Gly Ile Leu);

SEQ ID NO.:7 is a nucleic acid sequence encoding SEQ ID NO.:2; (ATCATCTCTGCGGTGGTTGGCATTCTG)

SEQ ID NO.:8 is a fully degenerate oligonucleotide capable of encoding SEQ ID NO.:2;(ATHATHAGYGCNGTNGTNGGNATHTTR)

SEQ ID NO.:9 is a fully degenerate oligonucleotide capable of encoding SEQ ID NO.:2;(ATHATHTCHGCNGTNGTNGGNATHTTR)

SEQ ID NO.:10 is a fully degenerate oligonucleotide capable of encoding SEQ ID NO.:2;(ATHATHAGYGCNGTNGTNGGNATHCTN)

SEQ ID NO.:11 is a fully degenerate oligonucleotide capable of encoding SEQ ID NO.:2;(ATHATHTGNGCNGTNGTNGGNATHCTN)

SEQ ID NO.:12 is a peptide used in the A2.1 binding assay; Phe Leu Pro Ser Asp Tyr Phe Pro Ser Val.

DESCRIPTION OF THE INVENTION

A. ISOLATED PEPTIDE SEQUENCES

One aspect of the invention is an isolated, antigenic peptide fragment that is a portion of the protein product of an oncogene and that is of sufficient size and amino acid composition to engage the binding cleft of an HLA-A2 molecule. The term "engage" has its ordinary meaning of to interlock or mesh together.

The peptide is recognized by cancer-specific CTL's of different origins and stimulates proliferation of cancer-specific CTL's. The term, "proliferation" is meant to include growth and clonal selection of CTL's and encompasses other functional characteristics of CTL's, such as induction of cytotoxicity (as measured by, for example, the chromium release assay) and/or induction of cytokine release by the lymphocytes.

The term "antigenic" refers to the ability of the peptides of the invention to stimulate cell-mediated immune responses (i.e., proliferation of CTL's) and/or stimulate humoral immune responses (i.e. proliferation of antibodies from B-lymphocytes against the peptide).

The term "isolated", when applied to the antigenic peptides of the present invention means peptides: (i) encoded by nucleic acids using recombinant DNA methods; or (ii); synthesized by, for example, chemical synthetic methods; or (iii) separated from naturally-occurring biological materials, and then purified using protein analytical procedures; or (iv) associated with chemical moieties (e.g. peptides, carbohydrates, fatty acids, and the like) other than those associated with the antigenic peptide in its naturally-occurring state; or (v) that do not occur in nature. Isolated antigenic peptides of the invention include peptides expressed from nucleotide sequences encoding the peptide or from a recombinant vector containing nucleotide sequences encoding the peptide (see below).

Preferred antigenic peptides of the invention are gene product fragments of the HER2/neu oncogene (also called c-erb2). See Coussens et al. supra for sequence of the HER2/neu protein, incorporated herein by reference. HER2/neu protein is expressed in normal tissues but is also amplified and overexpressed in tumor cells.

Because the HER2/neu peptides of the invention are particularly useful in initiating tumor-specific CTL proliferation (see Example 5), initiation of CTL action against normal, host cells and tissues is of concern. Preferred peptides of the invention are derived from tumor cells and are referred to as "mutant" peptides (i.e., expressed in tumor cells and tissues). The term "mutant" also refers to the fact that many peptides of the invention have one or more point mutations in their amino acid sequence as compared to "wild type" (i.e., normal) sequences.

Mutant peptides are preferentially associated with tumor tissue relative to normal tissues. For example, oncogene products are often overexpressed in tumor tissues, but not in normal (i.e. non-tumor) tissues. Peptides derived from such overexpressed oncogene products would be more likely to be presented on the surface of a tumor cell than on the surface of a normal cell and would therefore be "preferentially associated" with tumor tissue.

Particularly preferred are antigenic peptides that are associated only with tumor tissue. For example, as is the case with HER2/neu, oncogene products produced in tumor tissues sometimes bear mutations not found in non-tumor tissues. In some instances, mutant oncogene products will contain peptides that can be presented in association with an HLA-A2 molecule, and that are not found in the corresponding "normal" oncogene product. Such mutant peptides would therefore be associated only with tumor tissues and, like the mutant HER2/neu peptide described above, represent particularly preferred embodiments of the present invention.

Preferred antigenic peptides described herein are the gene product fragments of oncogenes expressed in a variety of tumor cells. In the case of the HER2/neu oncogene, it is expressed in many epithelial tumors, including breast (Slamon et al.; Science, 244:707–712, 1989), ovarian (Ioannides, et al., Cell. Immunol. 151:225, 1993), and gastric (Yamamoto et al., Nature, 319:230, 1986).

This invention is based, in part, on our discovery that HER2/neu antigenic peptides described herein, when presented by HLA-A2 molecules, are recognized by cancer-specific cytotoxic T lymphocytes from many different tumors. Thus, the preferred antigenic peptides of the invention may be widely recognized since 50% of the population is HLA-A2$^+$ and many different tumors express HER2/neu. See Examples 3 and 5. Moreover, we have discovered that at least one of these peptides derived from a fragment of the HER2/neu oncogene protein involves a point mutation found in the transmembrane portion of the tumor-derived HER2/neu protein and is not expressed in normal tissue.

1. HLA-A2 Binding Requirements

Presentation of antigenic peptides bound to human leukocyte antigen (HLA) class 1 molecules is a prerequisite for stimulation of cytotoxic T lymphocyte reactions and cytokine release. See Examples 4 and 5. The structural characteristics of the antigenic peptides are therefore strictly constrained by the requirement that they engage with the binding cleft of the histocompatibility leukocyte antigen (HLA), HLA-A2.

Certain binding requirements for HLA-A2 are well-characterized. Recent studies show that the majority of peptides binding to MHC class 1 molecules, in particular HLA-A2 molecules, have a size of 9–10 amino acids and require free N- and C-terminal ends. Thus, a peptide "fragment" of the invention is no greater than 10 amino acids long and is most preferably 9 amino acids long. Amino acid sequences longer than 10-mer (see for example, Ioannides, supra) will likely not engage the binding cleft at all. In addition to this size constraint, the HLA-A2 binding cleft requires two aliphatic hydrophobic anchor residues within the peptide ligand, these being leucine (L) at position 2 and L or valine (V) at the C-terminal end. See Falk et al., Nature, 351:290–296, 1991, incorporated herein by reference.

The role of nonanchor residues in determining HLA-A2 binding has recently been investigated. See Ruppert et al., Cell, 71:929–937, 1993, incorporated herein by reference. Amino acid residues strongly associated with good binding by HLA-A2 have been analyzed so that the number and sequence of possible 9-mer and 10-mer antigenic peptides of the invention is further constrained within narrow limits. The following Table, adapted from Ruppert et al., id, lists those amino acid residues associated with good binding of any 9-mer and 10-mer peptides to the binding cleft of HLA-A2.

| 9-Mer Peptides | | | | | | | | |
|---|---|---|---|---|---|---|---|---|
| POSITION: | | | | | | | | |
| 1 | 2 | 3 | 4 | 5 | 6 | 7 | 8 | 9 |
| Y | L,M | Y | S | Y | | A | P | L,V,I |
| F | | F | T | F | | | | |
| W | — | W | C | W | | | | |

| 10-Mer Peptides | | | | | | | | | |
|---|---|---|---|---|---|---|---|---|---|
| POSITION: | | | | | | | | | |
| 1 | 2 | 3 | 4 | 5 | 6 | 7 | 8 | 9 | 10 |
| A | L,M | L | G | | G | | Y | | L,V,I |
| Y | | V | | | | | F | | |
| F | | I | | | | | W | | |

| W | M | L |
|---|---|---|
|   |   | V |
|   |   | I |
|   |   | M |

Ruppert et al., supra, also discusses which residues are not desirable at each position of an HLA-A2-binding peptide.

2. Mutant peptide fragments

In the transmembrane portion of the corresponding rat neu gene there is a single point mutation (glutamic acid for valine) at residue 659 which enables this rat gene to transform the cell. See Bargmann et al. EMBO J., 7:2043, 1988.

When the transmembrane region (amino acids 654 to 662) of the human HER2/neu protein from breast cancer tissue was investigated for a transforming mutation, no corresponding glutamic acid for valine substitution was found. However, a neutral change of isoleucine (I) for valine (V) at position 655 was located as compared to the wild-type HER2/neu amino acid sequence. This substitution was tested for its transforming properties and no demonstrable transforming properties were found. See Slamon et al., supra.

This substitution was also found by DiFiore et al. (Science, 237:178–182, 1987) when they reconstructed a full length cDNA from previously derived overlapping clones which came from breast cancer cell lines. Moreover, Yamamoto et al. (Nature: 319:230–234, 1986) described a gastric cancer-derived full-length sequence that also contained the substitution at position 655. Therefore, it appears that the HER2/neu protein expressed in cancer tissue or cell lines contains the mutation at 655 as compared to the wild-type sequence described by Coussens et al. derived from normal tissue.

We have discovered a correlation between HER2/neu expression and cytotoxic lymphoyte recognition by transfecting an HLA-A2$^+$ melanoma with the HER2/neu gene rendering it recognizable to ovarian cancer-specific cytotoxic T-lymphocytes (CTL's). See Example 3.

In order to address the question of whether the HER2/neu is actually the source of the antigenic peptides recognized by the CTL's, the known amino acid sequences of HER2/neu (Coussens, et al., supra; Slamon et al., supra) were hand searched for nine-mer peptides containing the known canonical HLA-A2 position 2 and position 9 binding motifs.

Results of this search reveal that the known HER2/neu amino acid sequences from tumor cells all have the identical mutant peptide sequence, IISAVVGIL: SEQ ID NO.:2. This mutant peptide has the HLA-A2 anchor binding residue basic structure xIxxxVxxL (SEQ ID NO.:3) where I at position 2 is the mutation (HER2/neu position 655). This canonical sequence is not found between amino acids 654 and 662 of the wild-type HER2/neu oncogene protein (SEQ ID NO.:1) and the normal peptide is not predicted to engage with the HLA-A2 binding cleft. See Coussens et al., supra.

Therefore, in cancer SEQ ID NO. 2 and 3 would be a potential site of recognition since this amino acid sequence would appear foreign to the immune system. The basic structure of SEQ ID NO.:3 is identical to that for the influenza matrix peptide 58–66 (Bednarak et al., J. Immunol., supra, incorporated herein by reference) which has been shown to bind the HLA-A2 molecule.

We constructed a synthetic peptide (SEQ ID NO.:2: "GP2") and demonstrated recognition of this peptide by T-lymphocytes educated with autologous tumor (See Example 5).

Therefore, antigenic peptides of the invention include, but are not limited to, those containing as a primary amino acid sequence all residues substantially as depicted in SEQ ID NO.:2. These antigenic peptides are capable of inducing proliferation of cancer specific CTL's when the peptides are presented by the HLA-A2 binding cleft on T2 cells. See also Example 5.

Another sequence (proLeuThrSerIleIleSerAlaVal): SEQ ID NO.:4: "GP1") was synthesized and includes the isoleucine for leucine change placed at position 6 in the 9-mer peptide. Position 6 is less critical since SEQ ID NO.:4 is predicted to bind with or without the mutation as shown by Ruppert et al. We have shown that SEQ ID NO.:4 is not recognized by T-lymphocytes. See Example 5.

3. Functional equivalents

The stringent binding rules developed for HLA-A2 binding (Ruppert et al., supra) will also now allow persons having ordinary skill in the art to obtain isolated antigenic peptide sequences in which functionally equivalent amino acid residues are substituted for residues within SEQ ID NOS.:2 and/or 3, resulting in a functionally silent change. For example, SEQ ID NO.:5 is the functional equivalent of the mutant HER2/neu peptide of SEQ ID NO.:2 in which the isoleucine (I) at position 1 has been substituted with a tyrosine (Y) as allowed in the Table. Similarly, SEQ ID NO.:6 is the functional equivalent of mutant HER2/neu peptide SEQ ID NO.:2 in which position 1 is occupied by the phenylalanine (F). The canonical sequence of SEQ ID NO.:3, in conjunction with the Table, allows 4 positions to be filled with four amino acid residues each (I,Y,F and W each at positions 1,3,4, and 5) and 2 positions to be filled with two amino acid residues each (G,A at position 7 and I,P at position 8). It will therefore be readily appreciated that there are a total of 1,024 ($4^4 \times 2 \times 2$) variants of SEQ ID NO.:3.

Thus, according to the invention, an amino acid sequence is "functionally equivalent" compared with the sequence depicted in SEQ ID NO.2, if that amino acid sequence differs from the amino acid sequence depicted in SEQ ID NO.2 in that one or more of the amino acid residues of SEQ ID NO.2 has been substituted by another amino acid such that the relationship between the different amino acid sequences results in functional characteristics that are substantially the same.

That is, a "functional equivalent" of SEQ ID NO.:2 will also elicit the identical qualitative T-lymphocyte responses of initiating CTL proliferation, cell cytotoxicity, and cytokine production. Substitutions of particular amino acids (See Table) at non-anchor positions 1,3,4,5,6,7, and/or 8 of the 9-mer antigenic peptide of SEQ ID NO.:2 may be tested for functioning and may not produce radical changes in the physical and chemical characteristics of the mutant peptide, in which case mutant peptides containing the substitution would be considered to be functionally equivalent to peptides lacking the substitution. Functionally equivalent substitutes for an amino acid within the mutant HER2/neu antigenic peptide binding sequence of SEQ ID NO.:2 may therefore be selected from the Table. Significantly, the substitutions can be chosen for their effect on: (i) maintaining the structure of the peptide backbone in the area of the substitution, for example, as a sheet or helical conformation; (ii) maintaining the charge or hydrophobicity of the molecule at the substitution position; or (iii) maintaining the bulk of the side chain.

When it is difficult to predict the exact effect of the substitution in advance of doing so, one skilled in the art will appreciate that the effect can be evaluated using routine screening assays as described herein and known in the art. For example, HLA-A2 binding affinity may be tested by the procedures summarized in Example 1.

Similarly, antigenic properties may be tested by routine methods. A change in the immunological character of an antigenic peptide of the invention, such as binding to a given antibody, can be measured by an immunoassay such as a competitive type immunoassay. The functional equivalence of two peptide sequences can also be assessed by examining physical characteristics (e.g. homology to a reference sequence, the presence of unique amino acid sequences, etc.) and/or functional characteristics analyzed in vitro or in vivo. For example, functional equivalents of the mutant peptides of SEQ ID NO.:2 would be expected to otherwise behave like TAA's in other assays herein described or known in the art.

4. Isolated peptides of other oncogenes

The information provided on the HER2/neu mutant peptides described above allows the development of a general protocol for isolating any other oncogene-derived peptides that are capable of binding to the HLA-A2 cleft. In particular, peptides containing the canonical sequences (e.g., SEQ ID NO.: 3) can easily be identified. For example, known oncogene products can be scanned by eye, or with the aid of a computer program such as Genetics Computer Group, Sequence Analysis Software Package, version 7.2, 575 Science Drive, Madison, Wis., to identify peptides with the canonical sequences. This particular software package will scan the following databases (PIR-protein:11/93; SwissProt:8/93; Gen Pept:10/93; Gen Bank:12/93; EMBL Modified:6/93; Vecbase:8/87; TFDAA:7/92; and Prosite:11/93).

5. Altered peptides

The antigenic peptides of the invention can be altered to produce altered peptides that are capable of eliciting a stronger immune response against the original peptide than the original peptide is capable of eliciting against itself. Substitutions in, for example, SEQ ID NO.:2 that could be expected to produce increased antigenicity are those in which nonessential residues causing adverse interactions are replaced with those that enhance the antigenic function. One approach is to dissect the peptide, identify the individual residues within the peptide that either bind to the HLA-A2 molecule cleft or interact with the TCR, and to determine which residues are just spacers whose role may be filled by many different amino acids. See Berzofsky, "Epitope Selection and Design of Synthetic Vaccines", Ann. N.Y. Acad. Sci., 690:256–264 (1993), incorporated herein by reference.

For example, peptides of the invention that are capable of engaging with an HLA-A2 binding cleft might not engage optimally with that cleft. As discussed above, Ruppert et al., supra, have identified desirable and non-desirable amino acid residues for each position of an HLA-A2-binding peptide. Also, the statistical data presented by Falk et al., supra, provides indications of which amino acid residues are desirable and non-desirable at individual positions of an HLA-A2-binding peptide. Peptides of the invention that have the canonical HLA-A2-binding sequence, which specifies the amino acid residues allowed at the HLA-A2 anchor positions, might still have non-desirable residues at non-anchor positions, and therefore might not elicit as potent an immune response as would a peptide with more desirable amino-acid residues at non-anchor positions.

One of ordinary skill in the art would readily recognize that peptides of the invention could be altered, in that non-desirable amino acid residues at non-anchor positions could be substituted with desirable amino acids, as defined by Ruppert et al., supra, and Falk et al., supra, to create an altered peptide. One of ordinary skill in the art will further recognize that, where the information presented by Falk et al. and Ruppert et al. is in conflict, the information presented by Ruppert et al. is more likely to be reliable since Ruppert et al. performed direct binding studies whereas Falk et al. performed only statistical analyses of bound peptides.

Altered peptides could be tested for their ability to engage with an HLA-A2 binding cleft and/or to elicit an immune response against the original peptide by the methods disclosed herein. Most preferably, the altered peptides would be tested for their ability to stimulate proliferation of cytotoxic T-cells directed against the original peptide.

In particular, the mutant HER2/neu peptide of SEQ ID NO.:2 could be altered so that non-desirable amino acids at non-anchor positions are replaced with desirable amino acids. SEQ ID NO.:2 contains non-desirable amino acid residues, as defined by Falk et al., supra, at position 3 (a serine residue) and at position 5 (a valine residue). Preferred altered peptides of the invention have an amino acid sequence that differs from the amino acid sequence of SEQ ID NO.:2 in that (i) the serine residue at position 3 of SEQ ID NO.:2 has been substituted with a different residue, preferably not aspartic acid, glutamic acid, arginine, lysine, or histidine; and/or (ii) the valine residue at position 5 of SEQ ID NO.:2 has been substituted with a different residue, preferably tyrosine, phenylalanine, or tryptophan.

The HER2/neu mutant peptide of SEQ ID NO.:2 is difficult to work with due to its hydrophobicity (See Example 2). It may therefore be useful to make altered peptides that have an amino acid sequence that differs from the amino acid sequence of SEQ ID NO.:2 in that at least one hydrophobic non-anchor residue is substituted with a less-hydrophobic residue that has not been defined by Ruppert et al. as non-desirable at that position. The hydrophobicity of different amino acid residues is a well-defined property known in the art and presented in standard texts such as Current Protocols in Immunology, vol.2, (eds.) J. E. Coligan et al., J. Wiley & Sons, New York, N.Y., incorporated herein by reference.

6. Synthesis and purification of peptides

The peptides of the invention may be prepared by recombinant nucleotide expression techniques or by chemical synthesis using standard peptide synthesis techniques. For example, antigenic peptides of the invention can be produced, for example, by expressing cloned nucleotide sequences of the invention (see below). Alternatively, peptides of the invention can be generated directly from intact oncogene protein products. Peptides can be specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved peptide fragments are generated by preventing cleavage at a site which is susceptible to a proteolytic enzyme. For example, reaction of the ε-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1:401 (1962).

Peptides of the invention also can be modified to create peptide linkages that are susceptible to proteolytic enzyme catalyzed hydrolysis. For example, alkylation of cysteine residues with β-halo ethylamines yields peptide linkages that are hydrolyzed by trypsin. Lindley, Nature, 178:647 (1956). In addition, chemical reagents that cleave peptide chains at specific residues can be used. Withcop, Adv.

Protein Chem. 16:221 (1961). For example, cyanogen bromide cleaves peptides at methionine residues. Gross & Witkip, J. Am Chem Soc., 83:1510 (1961). Thus, by treating full-length oncogene peptides with various combinations of modifiers, proteolytic enzymes and/or chemical reagents, numerous discrete overlapping peptides of varying sizes are generated. These peptide fragments can be isolated and purified from such digests by chromatographic methods.

Most preferably, isolated peptides of the present invention can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.*, 23:451 (1967). See also Example 2. The antigenic activity of these peptides may conveniently be tested using, for example, the assays as described herein.

Once an isolated peptide of the invention is obtained, it may be purified by standard methods including chromatography (e.g., ion exchange, affinity, and sizing column chromatography), centrifugation, differential solubility, or by any other standard technique for protein purification. For immunoaffinity chromatography, a mutant HER2/neu peptide may be isolated by binding it to an affinity column comprising antibodies that were raised against that peptide, or a related peptide of the invention, and were affixed to a stationary support. Alternatively, affinity tags such as hexa-His (Invitrogen), Maltose binding domain (New England Biolabs), influenza coat sequence (Kolodziej et al. Methods Enzymol. 194:508–509, 1991), and glutathione-S-transferase can be attached to the peptides of the invention to allow easy purification by passage over an appropriate affinity column. A DNA affinity column using DNA containing a sequence encoding the peptides of the invention could be used in purification. Isolated peptides can also be physically characterized using such techniques as proteolysis, nuclear magnetic resonance, and x-ray crystallography.

Also included within the scope of the invention are antigenic peptides that are differentially modified during or after translation, e.g., by phosphorylation, glycosylation, crosslinking, acylation, proteolytic cleavage, linkage to an antibody molecule, membrane molecule or other ligand, (Ferguson, et al., Ann. Rev. Biochem. 57:285–320, 1988).

B. ISOLATED NUCLEIC ACID SEQUENCES

Another aspect of the invention is isolated nucleic acid sequences that encode the antigenic peptides described herein.

With regard to nucleic acid sequences of the present invention, "isolated" means: an RNA or DNA polymer, portion of genomic nucleic acid, cDNA, or synthetic nucleic acid which, by virtue of its origin or manipulation: (i) is not associated with all of a nucleic acid with which it is associated in nature (e.g. is present in a host cell as a portion of an expression vector); or (ii) is linked to a nucleic acid or other chemical moiety other than that to which it is linked in nature; or (iii) does not occur in nature. By "isolated" it is further meant a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and gel separation.

The nucleic acid sequences of the present invention may be characterized, isolated, synthesized and purified using no more than ordinary skill. See Sambrook et al., Molecular Cloning, Cold Spring Harbor Press, New York, 1989, incorporated herein by reference.

1. Functional equivalents

The term "functional equivalent", when applied to the nucleotide sequences of the invention, describes a sequence that satisfies one of the following conditions: (i) the nucleotide sequence in question can hybridize to a naturally-occurring mutant HER2/neu oncogene sequence, but it does not necessarily hybridize to that oncogene sequence with an affinity that is the same as that of the naturally occurring, mutant HER2/neu oncogene sequence; (ii) the nucleotide sequence in question can serve as a probe to distinguish between nucleotide sequences that contain the canonical HLA-A2 binding cleft sequences and those that do not (i.e, mutant HER2/neu oncogenes and wild-type HER2/neu oncogene sequences).

Due to the degeneracy of nucleotide coding sequences (see Alberts et al., Molecular Biology of the Cell, Garland Publishing, New York and London, 1989— page 103, incorporated herein by reference), a number of different nucleic acid sequences may be used in the practice of the present invention. These include, but are not limited to, sequences comprising SEQ ID NO.:7 (encoding the mutant HER2/neu amino acid sequence of SEQ ID NO.:2) and that have been altered by the substitution of different codons encoding the same amino acid residue within the sequence, thus producing a silent change. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character.

For example, several different nucleotide sequences are capable of encoding the amino acid sequence of SEQ ID NO.:2 which is the mutant HER2/neu mutant peptide, and SEQ ID NO.:1, which is the wild type HER2/neu peptide. Nucleotide sequences capable of encoding the mutant HER2/neu peptide can be summarized as the sequence 5'-3' (SEQ ID NOS.:8–11), where Y represents C or T/U, H represents A,C or T/U, R represents A, G, and N represents A, C, G, or T/U. Such degenerate nucleotide sequences are regarded as functional equivalents of the specifically claimed sequences. Nucleic acid sequences encoding the 1,024 functional equivalents of the canonical peptide sequence (SEQ ID NO.:3) are also included within the scope of the invention.

The nucleotide sequences of the invention (e.g. SEQ ID NOS.:7–11) can be altered by mutations such as substitutions, additions or deletions that provide for functionally equivalent nucleic acid sequence. In particular, a given nucleotide sequence can be mutated in vitro or in vivo, to create variations in coding regions and/or to form new restriction endonuclease sites or destroy preexisting ones and thereby to facilitate further in vitro modification. Any technique for mutagenesis known in the art can be used including, but not limited to, in vitro site-directed mutagenesis (Hutchinson, et al., J. Biol. Chem. 253:6551, (1978), use of TAB® linkers (Pharmacia), PCR-directed mutagenesis, and the like. The functional equivalence of such mutagenized sequences, as compared with un-mutagenized sequences, can be empirically determined by comparisons of structural and/or functional characteristics.

2. Isolated nucleic acid sequences of other oncogenes

The information provided on the HER2/neu mutant sequences described above allows the development of a general protocol for isolating any other oncogene nucleotide sequences encoding peptides that are capable of binding to the HLA-A2 cleft. In particular, nucleic acids encoding peptides containing the canonical sequences (e.g., SEQ ID NOS.:3) can easily be identified and synthetic oligonucleotides produced using well-known methods.

Alternately, it could be valuable to perform PCR reactions using as a DNA template a nucleotide sequence known to contain at least one nucleotide sequence that encodes a functional equivalent of SEQ ID NO.2 or 3. By way of example only, SEQ ID NOS.:8–11 are degenerate oligonucleotides that may be used as PCR primers to isolate nucleotide sequences from other oncogenes that contain sequences encoding the canonical mutant peptide sequences described herein. For instance, PCR may be performed in 25 ul volumes with 10mM Tris buffer pH8.5, 50mM KCL, 3mN $MgCl_2$, 0.01% gelatin, 50 uM each dNTP, 1.5 unit Taq DNA polymerase, 5 pM each primer and 0.4 ug human DNA from breast cancer tissue with 30 cycles of 30 seconds at 94° C., 30 seconds at 55° C. and 1 minute at 72° C. Preferred clones of a nucleotide sequence that encodes a mutant antigenic peptide of the invention includes clones of any eukaryotic nucleotide sequence capable of encoding at least SEQ ID NO.2.

3. Association with vector sequences

The isolated nucleotide sequences of the invention may be cloned or subcloned using any method known in the art (See, for example, Sambrook, J. et al., Molecular Cloning, Cold Spring Harbor Press, New York, 1989), the entire contents of which are incorporated herein by reference. In particular, nucleotide sequences of the invention may be cloned into any of a large variety of vectors. Possible vectors include, but are not limited to, cosmids, plasmids or modified viruses, although the vector system must be compatible with the host cell used. Viral vectors include, but are not limited to, lambda, simian virus, bovine papillomavirus, Epstein-Barr virus, and vaccinia virus. Viral vectors also include retroviral vectors, such as Amphotrophic Murine Retrovirus (see Miller and Rosman Biotechniques 7:980–990, 1984, incorporated herein by reference). Plasmids include, but are not limited to, pBR, pUC, pGEM (Promega), and Bluescript® (Stratagene) plasmid derivatives. 4. Introduction into and expression in host cells Recombinant vectors containing eukaryotic nucleotide sequences that encode mutant HER2/neu peptides of the invention can be introduced into host cells by, for example, transformation, transfection, infection, electroporation, etc. See Examples 3 and 7.

Recombinant vectors containing nucleotide sequences encoding the mutant HER2/neu peptide of the invention can be engineered such that the eukaryotic nucleotide sequences are placed under the control of regulatory elements (e.g. promoter sequences, polyadenylation signals, etc.) in the vector sequences. Such regulatory elements can function in a host cell to direct the expression and/or processing of nucleotide transcripts and/or peptide sequences of the invention.

Expression systems can utilize prokaryotic and/or eukaryotic (i.e., yeast, human) cells. See, for example, "Gene Expression Technology", Volume 185, *Methods in Enzymology*, (ed. D. V. Goeddel), Academic Press Inc., (1990) and U.S. Pat. No. 5,229,115 "Adoptive Immunotherapy with Interleukin-7" (Lynch: Jul. 20, 1993) incorporated herein by reference. A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11–195, V. 185, *Methods in Enzymology*, supra; see also Hawley, D. K., and McClure, W. R., "Compilation and Analysis of *Escherichia coli* promoter DNA sequences", Nucl. Acids Res., 11:4891–4906 (1983), both of which are incorporated herein by reference. Expression of peptides of the invention in a recombinant bacterial expression system can be readily accomplished.

Yeast cells suitable for expression of the mutant peptides of the invention include the many strains of *Saccharomyces cerevisiae* (see above) as well as *Pichia pastoris*. See, "Heterologous Gene Expression in Yeast", Section IV, pp. 231–482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485–596, V. 185, *Methods in Enzymology*, supra, incorporated herein by reference.

Suitable expression systems include those that transiently or stably express DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant molecules can be introduced into host cells via transformation, transfection, infection, electroporation, etc. Generally, expression of the mutant peptides of the invention in a host is accomplished using a vector containing DNA encoding the peptide under the control of regulatory regions that function in the host cell.

In particular, expression systems that provide for overproduction of a nucleotide sequence encoding the mutant HER2/neu peptides of the invention can be prepared using, for example, the methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a eukaryotic gene) into which a nucleotide sequence capable of encoding a mutant HER2/neu peptide can be inserted; (2) the promoter of this eukaryotic gene; and (3) a second promoter located upstream from the eukaryotic gene promoter which overrides the eukaryotic gene promoter, resulting in overproduction of the mutant HER2/neu peptide. The second promoter is obtained in any suitable manner. Possible host cells into which recombinant vectors containing nucleotide sequences can be introduced include, for example, bacterial cells, yeast cells, non-human mammalian cells in tissue culture or in situ, and human cells in tissue culture but not in situ. Nucleotide sequences that have been introduced into host cells for encoding the mutant HER2/neu peptides of the invention can exist as extrachromosomal sequences or can be integrated into the genome of the host cell by homologous recombination, viral integration, or other means. Standard techniques such as Northern blots and Western blots can be used to determine that introduced sequences are in fact being expressed in the host cells.

In one method of expressing a human HER2/neu peptide, a cDNA clone that contains SEQ ID NO.:2 is cloned into a expression vector and transfected into T2 cells ( See also Example 7). Expression is monitored after transfection by, for example, Northern, Southern, or Western blotting.

C. ANTIBODIES

The term "antibodies" is meant to include monoclonal antibodies, polyclonal antibodies and antibodies prepared by recombinant nucleic acid techniques that are selectively reactive with peptides of the present invention. The term "selectively reactive" refers to those antibodies that react with one or more antigenic determinants of a peptide and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

In particular, antibodies may be raised against amino-terminal (N-terminal) or carboxy-terminal (C-terminal) residues of the mutant HER2/neu peptide of the invention.

Generally, to isolate antibodies to a mutant HER2/neu peptide of the invention, peptide SEQ ID NO.:2 or its functional equivalent may be selected as an immunogen. This peptide immunogen can be attached to a carrier to enhance the immunogenic response. Although the peptide immunogen can correspond to the mutant HER2/neu peptide of the invention, certain amino acid sequences are more likely than others to provoke an immediate response, for example, the C-terminal amino acid of the mutant HER2/neu peptide of the invention.

Other alternatives to preparing antibodies that are reactive with a mutant HER2/neu peptide of the invention include: (i) immunizing an animal with a protein expressed by a prokaryotic (e.g., bacterial) or eukaryotic cell; the cell including the coding sequence for all or part of a mutant HER2/neu peptide; or (ii) immunizing an animal with whole cells that are expressing all or a part of a mutant HER2/neu peptide. A cDNA clone encoding, for example, a mutant HER2/neu peptide of the present invention may be expressed as a fusion protein in a host using standard techniques (see above; see Sambrook et al., Molecular Cloning; A Laboratory Manual, Cold Spring Harbor Press, Cold Spring Harbor, N.Y.: 1989) such that 5–20% of the total peptide that can be recovered from the host are mutant HER2/neu peptides of the invention. Recovered peptides can be electrophoresed using PAGE and the appropriate band can be cut out of the gel. The desired peptide sample can then be eluted from the gel slice and prepared for immunization. Alternatively, a mutant HER2/neu peptide of interest can be purified by using conventional methods such as, for example, ion exchange hydrophobic, size exclusion, or affinity chromatography.

Once the mutant HER2/neu peptide immunogen is prepared, mice can be immunized twice intraperitoneally with approximatively 50 micrograms of peptide immunogen per mouse. Sera from such immunized mice can be tested for antibody activity by immunohistology or immunocytology on any host system expressing the mutant HER2/neu and by ELISA with the expressed mutant HER2/neu peptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymac Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of peptides of the present invention may be analyzed in order to identify portions of amino acid sequence which may be associated with increased immunogenicity. For example, peptide sequences of the invention may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward peptides of the invention, any technique that provides for the production of antibody molecules by continuous cell lines may be used. For example, the hybridoma technique originally developed by Kohler and Milstein (Nature, 256:495–497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See also Akiyama et al. (Science, 232:1644–1646, 1986, incorporated herein by reference) who teaches preparation of antibodies against a synthetic 14 amino acid fragment of the wild-type HER2/neu gene product; and Larrick et al., U.S. Pat. No. 5,001,065 and references cited therein. Further, single-chain antibody (SCA) methods are also available to produce antibodies against peptides of the invention (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to antibodies against, for example, mutant HER2/neu peptides or can be coupled to the mutant HER2/neu peptides themselves. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the mutant HER2/neu peptide and another molecule so long as the two moieties retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." Jour. Immun. 133:1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185–216; and Vitetta et al., supra).

Preferred linkers are described in the literature. See, for example, Ramakrishnan, S. et al., Cancer Res. 44:201–208

(1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. 24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

D. DIAGNOSTIC APPLICATIONS

The known sequences of the peptides of the present invention now permit the screening of any cell sample for the expression of these peptides. For example, peptides may be extracted from the surface of cells and exposed in a Western blot to antibodies selectively specific for the peptides of the invention. The presence of a positive signal is indicative of cells carrying the antigenic peptide. In another technique, total RNA is isolated from cultured cells or tissues by, for instance, the guanidium method. See Current Protocols in Immunology, supra. Poly(A+) RNA is separated from total RNA using an oligo(dt) cellulose column. The bound poly(A+)RNA is eluted by removing salt from the solution, thus destabilizing the dT:RNA hydrid. Poly(A+)RNA is then transcribed into DNA using reverse transcriptase. The obtained DNA is amplified by PCR using two DNA primers. A set of PCR primers is selected, one primer hybridizing to the DNA sequences downstream of the HER2/neu mutation and one DNA primer hydridizing upstream of the mutation. Thus, only the DNA segment overlapping the mutation will be amplified by PCR. Nucleotide sequencing of the PCR product demonstrates whether the cell sample expresses wild-type or mutated HER2/neu. It is possible to select DNA primers such that only the mutant DNA will be amplified, not the wild-type.

E. IMMUNOTHERAPEUTIC APPLICATIONS

1. Compositions

The nucleotide sequences and polypeptides expressed by the sequences described herein can be used in pharmaceutical compositions in, for example, adoptive immunotherapy, peptide vaccine therapy and/or gene therapy. An exemplary pharmaceutical composition is a therapeutically effective amount of mutant HER2/neu nucleotide sequence of the invention or a mutant HER2/neu antigenic peptide optionally included in a pharmaceutically-acceptable and compatible carrier. The term "pharmaceutically-acceptable and compatible carrier" as used herein, and described more fully below, refers to (i) one or more compatible solid or liquid filler diluents or encapsulating substances that are suitable for administration to a human or other animal, and/or (ii) a system, such as a retroviral vector, capable of delivering, for instance, the mutant HER2/neu nucleotide sequence to a target cell. In the present invention, the term "carrier" thus denotes an organic or inorganic ingredient, natural or synthetic, with which the antigenic peptides and nucleic acid sequences of the invention are combined to facilitate application. Another exemplary carrier is, for example the T2 cell line (See Example 5) or other cells (e.g., fibroblasts)which may present on their surfaces the antigenic peptides of the invention.

The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration.

The term "compatible" as used herein, means that the components of the pharmaceutical compositions are capable of being commingled with the nucleic acid and/or peptides of the present invention, and with each other, in a manner such that there is no interaction that would substantially impair the desired pharmaceutical efficacy.

Dose of the pharmaceutical compositions of the invention will vary depending on the subject and upon particular route of administration used. By way of an example only, an overall dose range of from about 1 microgram to about 300 micrograms is contemplated for human use. This dose can be delivered on at least two separate occasions, preferably spaced apart by about 1 week. See for instance, Mitchell, M. S. et al., Cancer Res., 48:5883–5893 (1988), incorporated herein by reference. Pharmaceutical compositions of the present invention can also be administered to a subject according to a variety of other, well-characterized protocols. For example, certain currently accepted immunization regimens can include the following: (i) a first dose at elected date; a second dose at 1 month after first dose; and a third dose at 5 months after second dose. See *Product Information, Physician's Desk Reference*, Merck Sharp & Dohme (1990), at 1442–43. (e.g., Hepatitis B Vaccine-type protocol); (ii) Recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See *Product Information, Physician's Desk Reference*, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The peptides of the invention may also be administered per se (neat) or in the form of a pharmaceutically acceptable salt. When used in medicine, the salts should be pharmaceutically acceptable but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulphuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acids and/or peptides of the invention together with one or more pharmaceutically acceptable carriers thereof and optionally any other therapeutic ingredients.

The compositions include those suitable for oral, rectal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. All methods include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acids and/or peptides of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the nucleic acids and/or peptides of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The nucleic acids and/or peptides of the present invention can also be conjugated to a moiety for use in vaccines. The moiety to which the nucleic acids and/or polypeptides is conjugated can be a protein, carbohydrate, lipid, and the like. See discussion of available linkers, supra. The chemical structure of this moiety is not intended to limit the scope of the invention in any way. The moiety to which nucleic acids and/or peptides may be bound can also be an adjuvant. The term "adjuvant" is intended to include any substance which is incorporated into or administered simultaneously with the nucleic acids and/or peptides of the invention which potentiates the immune response in the subject. Adjuvants include aluminum compounds, e.g., gels, aluminum hydroxide and aluminum phosphate gels, and Freund's complete or incomplete adjuvant. The paraffin oil may be replaced with different types of oils, e.g., squalene or peanut oil. Other materials with adjuvant properties include BCG (attenuated *Mycobacterium tuberculosis* plus other microbial derivatives), calcium phosphate, levamisole, isoprinosine, polyanions (e.g., poly A:U), leutinan, pertussis toxin, lipid A, saponins and peptides, e.g., muramyl dipeptide. Rare earth salts, e.g., of lanthanum and cerium, may also be used as adjuvants. The amount of adjuvant required depends upon the subject and the particular therapeutic used and can be readily determined by one skilled in the art without undue experimentation.

An exemplary composition of the invention can comprise a therapeutically effective amount of the isolated mutant peptide of the invention, either alone or in combination with an immunoadjuvant and/or carrier.

2. Methods of sensitizing lymphocytes in vitro

Current adoptive cancer immunotherapy procedures involve isolating tumor-infiltrating lymphocytes (TIL) from fresh surgical specimens, growing these TIL's to therapeutic numbers ($10^{10}$–$10^{11}$), and reinfusing these cells back into the patients. The intention is that these T-lymphocytes will demonstrate anti-tumor activity due to their prior in vivo stimulation and selection within the environment of the tumor from which they came. The term "isolated", when applied to a population of T-lymphocytes means T-lymphocytes separated from naturally-occurring biological materials (See Examples 3 and 6) or associated with chemical moieties (e.g. peptides, carbohydrates, fatty acids, and the like) other than those associated with the T-lymphocytes in their naturally-occurring state.

Unfortunately, this in vivo activation is inefficient or the tumor would not exist. We have shown that the anti-tumor activity of TIL can be enhanced in vitro by repeatedly stimulating the TIL with autologous tumor. See Peoples et al. Surgery, 114:227 1993, incorporated herein by reference. This in vitro stimulation causes the preferential expansion of TIL's with specificity for the tumor, yet again this method is relatively inefficient because of the weak antigenicity of most tumors.

Since we have demonstrated that SEQ ID NO.:2 is recognized by TIL which have been stimulated with autologous tumor, this antigenic peptide must be expressed by these tumor cells. Examples 4 and 5. The peptide may be loaded in large quantities onto the T2 cell line or other cell line capable of presenting the peptide). These cells have the property that they express HLA-A2 bound with relatively few different peptides, because of an antigen presenting defect. These relatively few peptides may be competitively displaced by the antigenic peptides of this invention. The loaded T2 is very antigenic and, therefore, useful to stimulate TIL in vitro by repetitive stimulation as with autologous tumor.

We currently use TIL's because this population of T-lymphocytes are biased in vivo toward tumor recognition; however, to acquire these cells, the patient must undergo surgical resection of their tumor. The identification of the antigenic peptide of the invention makes it feasible to generate tumor-specific cytotoxic T lymphocytes (CTL) from peripheral blood lymphocytes (PBL) which are easily obtained from patients by simple phlebotomy. The PBL are cultured, for instance, with SEQ ID NO. 2 alone initially, then with autologous PBL pulsed with the peptide repeatedly as described by Bednarek et al., J. Immunol. 147:4047, incorporated herein by reference. See also Example 6. The resulting peptide-specific CTL's recognize the tumor efficiently when adoptively transferred in therapeutic numbers. Potentially, fewer cells would be required to elicit a clinical response making the therapy more timely, less cumbersome, and less costly.

3. Methods of sensitizing lymphocytes in vivo

Tumor vaccines are intended to stimulate the host immune system in vivo against the tumor of concern. These vaccines can be used as a therapeutic tool or preventative one. Currently, the majority of tumor vaccines are genetically-modified tumor cells designed to augment the host immune response against the tumor by either creating a more conducive tumor environment (i.e., tumor cells transfected with cytokine genes; See Golumbek, P. et al., Science 254:713–716, 1991, incorporated herein by reference) or making the tumor more antigenic (i.e., transfecting tumors with the costimulant, B7; See, Townsend and Allison, Science 259:368–370, 1993, incorporated herein by reference.).

There are clinical trials already underway to test these vaccines in patients with end-stage disease (Rosenberg, NCI, melanoma; Pardol, Johns Hopkins, renal cell carcinoma; Chang, Michigan, melanoma). Under Dr. Rosenberg's protocol, genetically modified tumor cells are injected into the patients' thigh and an immune response allowed to occur. The draining inguinal lymph nodes are then harvested (and the injection site resected) and these in vivo—sensitized lymphocytes cultured and used for adoptive transfer back into the patient.

Cells such as T2 (or carrier cells such as autologous fibroblasts or B cell lines) are pulsed with an antigenic peptide of the invention (See Example 5) and similarly injected to produce a local immune reaction. The draining lymph nodes are harvested as a source of peptide/tumor-specific CTL for adoptive transfer. With the peptide/T2 (or fibroblast or B cell line), as opposed to the tumor cells, the patient would be exposed to much less potential danger than injecting genetically modified, but still viable tumor cells. Furthermore, the injection site would not have be resected since the T2, fibroblast, or B cell lines pose no malignant risk to the patient. This broadens the choice of injection sites and simplifies the harvest procedure once again to the benefit of the patient.

A peptide-based tumor vaccine may be designed to promote active cellular protective immunity against certain cancers. Patients with previously treated malignancies but at high risk for recurrence (e.g., node-positive breast cancer) are a first obvious group to vaccinate, followed by those with predicted high risk factors for developing primary cancers. A peptide vaccine (e.g., containing SEQ ID NO.:2 in combination with a synthetic carrier such as beads) is delivered systemically and taken up by antigen-presenting cells (APC) which, in turn interact with the host CTL's. This method may be inefficient as much of the peptide would be degraded and not presented. Mitchell et al., however, have demonstrated an effective protocol using the adjuvant DETOX (Cancer Res. 48:5883; incorporated herein by reference). This adjuvant (Ribi ImmunoChem Res. Inc., Hamilton, MT) contains detoxified endotoxin (monophosphory) lipid A) from *Salmonella minnesota*, cell wall skeletons of *Mycobacterium phlei*, squalene and emulsifier.

The vaccine is delivered as mentioned above or loaded on a carrier cell like T2, autologous fibroblasts, or B cell lines which themselves post no risk to the patient. The peptide/HLA complex is then fixed on the cell surface (such as with paraformaldehyde treatment) to prevent the internalization of the complex.

Another way to insure peptide expression on the T2, autologous fibroblast, or B cell lines is to transfect the carrier cell with episomal vectors containing the short DNA sequence for the peptide as described by Bednarek et al., supra for the influenza virus matrix peptide. Other vectors have been also used including poxvirus vector (Paoletti et al., "Immunotherapeutic Strategies for Cancer Using Poxvirus Vectors," Ann. NY Acad. Sci.; 292–300 incorporated herein by reference) and vaccinia vector (Bernards et al., Proc. Natl. Acad. Sci. 84:6854; incorporated herein by reference).

A tumor vaccine consisting of a nonthreatening cell expressing high amounts of a peptide of the invention would elicit a protective cellular response. The patient is then protected against future assaults by tumors expressing the same peptide.

We have shown that HER2/neu mutant peptide is expressed and recognized by breast, ovarian cancer, and lung cancer TIL's. Together, these tumors account for 65% of all female malignancies. The fact that the HER2/neu mutation also exists in gastric cancer (Yamamoto et al., Nature 319:230) opens the possibility that the mutated peptide exists in other gastrointestinal malignancies known to express HER2/neu such as pancreatic and colon cancer. Furthermore, since the mutated HER2/neu peptide is not found in normal tissue, which expresses wild-type HER2/neu (Coussens et al., Science 230:1132: see also SEQ ID NO.:1), no destruction of normal tissue would be induced. Therefore, antigenic mutant peptides in general, and the mutant HER2/neu mutant peptides in particular, could form the basis of widely recognized, tumor-specific vaccines.

The invention will now be illustrated with the following non-limiting examples.

EXAMPLE 1

HLA-A2 Binding Assay

This Example illustrates a procedure adapted from Ruppert et al. (supra), for purifying HLA-A2 and performing a quantitative binding assay.

A2.1 Purification

The HLA-A2.1-positive human Epstein-Barr virus-transformed B cell line JY is used as a source of A2 molecules. In brief, cell lysates from large-scale ($10^{10}$–$10^{11}$) cell cultures are filtered through 0.45 µM filters and purified by affinity chromatography. Columns of inactivated Sepharose CL4B and protein A-Sepharose are used as precolumns. The cell lysate is subsequently depleted of HLA-B and HLA-C molecules by repeated passage over protein A-Sepharose beads conjugated with anti-HLA-B/C antibody to remove HLA-B and HLA-C molecules. Subsequently, the anti-HLA-A/B/C antibody W6/32 is used to capture HLA-A2.1 molecules. Molecules are eluted with diethylamine, 1% n-ocyl glucoside (pH 11.5), neutralized with 1 mM Tris (pH 6.8), concentrated by ultrafiltration on Amicon 30 cartridges, and stored at 4° C. Protein purity, concentration, and effectiveness of depletion steps are monitored by SDS-polyacrylamide gel electrophoresis.

A2.1 Binding Assay

A quantitative assay for A2.1-binding peptides based on the inhibition of binding of a radiolabeled standard peptide to detergent-solubilized MHC molecules is described. In brief, a standard peptide (SEQ ID NO.:12; FLPSDYFPSV) is iodinated by the chloramine T method (Buus et al., 1987, incorporated herein by reference). MHC concentrations yielding approximately 15% of bound peptide are used in the inhibition assays (usually in the 10 nM range). Various doses of the test antigenic peptides of the invention (ranging from 100 µM to 1 nM) are coincubated, together with the ~5 nM radiolabeled standard peptide and A2 molecules, for 2 days at room temperature in the presence of a cocktail of protease inhibitors and 1 µM $\beta_2$-microglobulin. The final concentrations of peptide inhibitors are 1 mM phenylmethylsulfonyl fluoride, 1.3 mM 1.10 phenanthroline, 73 µM pepstatin A. 8 mM EDTA, and 200 µM N-a-p-tosyl-L-lysine chloromethyl ketone. Final detergent concentration in the mixture is 0.05% Nonidet P-40. At the end of the incubation period, the percent of MHC-bound radioactivity is determined by gel filtration, and the 50% inhibitory dose calculated for each peptide, as described in Sette et al., 1992, J. Immunol. 148:844–851, incorporated herein by reference.

EXAMPLE 2

Peptide synthesis

Peptides are synthesized in the Biopolymer Laboratory at Brigham and Women's Hospital using solid phase techniques on an Applied Biosystems peptide analyser.

Syntheses are done by sequential coupling of N-a-Fmoc-protected amino acids on an Applied Biosystems 430A peptide synthesizer (Foster City, Calif.) using standard t-butoxylcarbonyl- and 9-fluoromethyloxycarbonyl-protected amino acids and resins. Resins are treated with acetic anhydride to block free, unreacted amino groups. Deprotection and removal of peptide from resins are performed as recommended by Applied Biosystems (430A Peptide Synthesizer Manual).

Crude products are dissolved in either water-acetic acid of DMSO-acetic acid mixtures. Solutes are filtered and injected onto C-18 semipreparative reverse phase HPLC columns (Waters Corp., Milford, Mass.) and eluted isocratically with TFA-acetonitrile gradients.

Identity and purity of the final products is established by amino acid analysis (Current Protocols in Immunology, supra) and mass spectrometry (Covey et al., Anal. Chem., 63: 1193, 1991). Purification is continued until single peaks were obtained by analytical HPLC (Current Protocols in Immunology, supra).

SEQ ID No.:2 was made about 40% pure by weight and it is extremely unlikely that a 9 amino acid peptide with a closely related but different sequence could be contaminating this peptide (personal communication, David Teplow, Director of Brigham and Women's Biopolymer Lab). Because SEQ ID NO.:2 is so hydrophobic, we experienced difficulties in dissolving it. We tried acetic acid, acetonitrile, and methanol all of which helped in dissolving the peptide but all of which interfered with standard chromium release assays primarily because of the effect of pH on the cells. Dilutions and mixtures of these solvents were also attempted. Finally, the peptides were dissolved as much as possible in water or HBSS with prolonged time (as long as 36 hrs) and vortexing.

EXAMPLE 3

Transfection of melanoma cell lines with the HER2/neu gene.

This example illustrates the first observation in a human tumor system that HER2/neu oncogene expression is related to induction of antigenicity.

1. Preparation of T lymphocytes and tumor cells

Patients. Six consecutive patients with the subsequently confirmed diagnosis of ovarian cancer and more than 100 ml ascites at operation provided both solid tumors (either from the ovary or omentum) and ascites. Specimens were obtained through the Gynecologic Oncology Department and Pathology Department at Brigham and Women's Hospital, Boston, Mass., under approval of the Institution Review Board. None of the patients had received chemotherapy, and materials were collected from the patients' initial operations in all cases. Similary, specimens from patients with confirmed breast cancer and non-small cell lung cancer were also obtained and processed, as described below.

Preparation of T cells and tumor cells. Solid tumor specimens were acquired from the pathologist after frozen section diagnosis and were transported to the laboratory, weighed, and processed immediately. The tumors were minced manually to fragments less than 1 $mm^3$ and then enzymatically digested into single cell suspension in 0.1% hyaluronidase, 0.01% deoxyribonuclease, and 2.5 units/ml collagenese (Sigma Chemical Company, St. Louis, Mo.) and 1 mmol/L HEPES buffer (Gibco Laboratories, Grand Island, N.Y.) in Hank's balanced salt solution (HBSS) (Gibco Laboratories) for 2 to 4 hours with continual stirring. Ascites fluid was collected in heparinized containers in the operation room, diluted 1:1 with HBSS without calcium or magnesium (Gibco Laboratories), and centrifuged at 200 g for 20 minutes to pellet the cells. Some ascites were centrifuged undiluted to freeze aliquots of sterilely filtered ascites for tumor cultures. Red blood cells and cell debris were removed from the ascites cell pellet by centrifugation over 100% Ficoll (Organon Teknika Corporation, Durham, N.C.) for 20 minutes. Finally, both single cell suspensions (from ascites and solid tumor) were washed twice and lymphocytes and tumor cells were separated by centrifugation on discontinuous 75%/100% Ficoll gradients. The lymphocytes were collected at the lower interface and tumor cells were collected at the upper interface. Both populations were washed twice with HBSS, checked for viability, and counted with trypan blue (Gibco Laboratories) exclusion. Aliquots of TAL, TIL, ascitic tumor, and solid tumor were frozen in 90% fetal calf serum (FCS) (Gibco Laboratories) and 10% dimethyl sulfoxide (Sigma Chemical Company) at −80° C. or used fresh.

Generation of tumor-specific CTL. TAL and TIL were suspended in complete lymphocyte medium composed of RPMI-1640 medium (Gibco Laboratories) with 20% Ventrex (Ventrex laboratories, Portland, Me.) and 10% FCS and supplemented with 50 units/ml penicillin and 50 µg/ml streptomycin (Gibco laboratories), 25 mmol/L HEPES buffer, and 2 mmol/L L-glutamine (Gibco Laboratories). Cultures were suspended at $5 \times 10^5$ cells/ml on solid phase anti-CD3 monoclonal antibody polystyrene plates (Orthoclone OKT3; Ortho Pharmaceutical Corporation, Raritan, N.J.) and placed in a humidified incubator at 37° C. in 5% $CO_2$. After 48 hours T cells were transferred to uncoated 25 $cm^2$ flasks (Costar, Cambridge, Mass.) and supplemented with 50 IU/ml IL-2 (AMGEN, Thousand Oaks, Calif.). IL-2 was added at 50 IU/ml every 3 days. Cells were washed, counted and resuspended in fresh complete lymphocyte medium at $5 \times 10^5$ cells/ml every week. At weeks 1, 3, and 5, autologous irradiated (10,000 rads) tumor cells were added at a 10:1 lymphocyte:tumor ratio. Ascitic tumor was used to feed TAL cultures and solid tumor was used to feed TIL cultures. Lymphocytes were maintained in culture up to 12 weeks. Weekly aliquots were frozen in 90% FCS and 10% dimethyl sulfoxide for future evaluation.

Generation of tumor cell lines. Ascitic tumor cells and solid tumor cells were cultured in 25 $cm^2$ flasks initially in RPMI-1640 medium plus 20% FCS. Cells were suspended at $1 \times 10^6$ cells/ml and were supplemented with insulin 5 µg/ml (Sigma Chemical Company) and for ascitic tumor, 10% by volume of sterilely filtered ascitic fluid. Insulin was added every 3 days and the medium was changed weekly. Cultures were trypsinized (0.05% trypsin and 0.02% ethylenediaminetetraacetic acid; Gibco Laboratories) when confluent and expanded. In some cases, fibroblasts were controlled with minimum essential medium (Gibco laboratories) with D-valine substituted for L-valine. Early passage cultured tumor cells were frozen in aliquots or used fresh when available as feeders and targets in cytotoxicity assays.

Phenotype analysis. TAL and TIL bulk cultures were sampled periodically for changes in T-cell phenotype. Five $\times 10^5$ cells were doubly labeled with a fluorescein- and a phycoerythrin-conjugated mAb (20 μl) for 30 minutes at 4° C. Monoclonal antibodies to CD3, T-cell receptor (TcR), CD4, CD8, CD16, and CD56 (Becton Dickinson, Mountain View, Calif.) were used for two color analysis on a Coulter Epics C cytometer (Coulter Electronic, Hialeah, Fla.).

Cytotoxicity assays. Cytotoxicity was determined by standard 4-hour chromium (Cr)-release assays. Briefly, fresh cryopreserved or early passage cultured tumor and the NK-sensitive K562 cell line were used as targets. Allogeneic ovarian targets came from the other patients in the study. Targets were labeled with 50 to 100 μCi sodium chromate-51 (New England Nuclear, Boston, Mass.) for 1 hour in a 37° C. water bath with frequent resuspension of cells. Effectors were plated in 96-well round bottom plates (Costar) at designated effector:target ratios (usually 80:1 to 10:1) in 100 μl/well. The plates were centrifuged at 80 g for 5 minutes and placed in a humidified incubator at 37° C. and 5% $CO_2$ for 4 hours. Culture supernatant was collected using a supernatant collection system (Skatron, Inc., Sterling, Va.) and radionuclide release was measured on a gamma counter (Gamma Tnc 1191; TM Analytic, Elk Grove, Ill.). All determinants were done in triplicate. Results are expressed as percentage specific lysis as determined by the equation % Lysis=[Experimental mean cpm—Spontaneous mean cpm] /[Maximum mean cpm—Spontaneous mean cpm]$\times \times 100$ or lytic units, defined as the number of effector cells needed to lyse 20% of the targets and expressed per $10^7$ cells ($LU_{20}/10^7$ cells).

Blocking of CTL activity by mAb

Target cells were incubated with 1/10-diluted supernatant of W6/32-producing hybridoma (anti-HLA class 1), L227-producing hybridoma (anti-HLA class 2) or BB7.2-producing hybridoma for 30 min at 4° C. after labeling with chromium. The mAb were added to the effector cells and target cells in ¼-dilution, and a 4 h-$^{51}$Cr-release assay was performed as described above.

In situ hybridization

A 1.6 kb human neu cDNA (hu-neu, Oncogene Science) and a control DNA (pBR322, Oncogene Science) were labeled with biotin using a BioNick™Labeling Kit (Gibco BRL) according to the instruction manual. Tumor cells (5 to $10\times10^4/100$ ml CM) were put on a poly-1-lysine-coated slide and incubated at 37° C. for 60 to 90 min. After washing with PBS, the plate was treated with 40 μg/ml of prewarmed proteinase K (Sigma) at room temperature (RT) for 2 min. The plate was serially treated with 4% paraformaldehyde for 1 min, 3×PBS for 3 min, 1×PBS for 6 min, and dehydrated through a graded ethanol series (50%, 70%, 90% and 100%) for 3 min each. Hybridization of the labeled probe to the tissue slide was performed by using the In Situ Hybridization and Detection System (Gibco BRL) according to the instruction manual. Briefly, 200 ng/ml hybridization buffer of the probe was put on the slide and incubated at 43° C. for 18 h. The slide was washed with 0.2× SSC for 20 min at RT and subsequently treated with 100 μl of blocking solution at RT for 15 min followed by addition of 100 μl of streptoavidin-alkaline phosphatase conjugate. After washing with tris-buffered saline (pH 7.5) for 30 min and with alkaline substrate buffer (100 mM Tris base, 150 mM NaCl, 50 mM $MgCl_2$, pH 9.5) for 5 min, the slide was incubated in alkaline substrate buffer mixed with 300 μg/ml of nitroblue tetrazolium and 166 μg/ml of 4-bromo-5-chloro-3-indolylphosphate at 37° C. for 90 min. The slide was washed with $H_2O$, dehydrated, mounted and observed with photomicroscopy.

Transfection of melanoma cells with the HER2/neu gene.

Transfection was performed by a lipofection method (Feigner et al., Proc. Nat. Acad. Sci., USA, 84:7413, 1987) as described in the manufacturers' instructions (Gibco, BRL). Briefly, $1\times10^5$ exponentially growing melanoma cells of two cell lines (A-MM and G-MM) were cultured in a 30-mm dish for 18 h in DMEM supplemented with 10% FCS. Five μg of the plasmid containing the HER2/neu gene (Yamamoto et al., Nature 319:230, 1986; incorporated herein by reference) and the SV40 promoter and 1 μug of pMoNeo (Colbere-Garapin et al., J. Mol. Biol.150:1, 1981) containing the neomycin phosphotransherase gene and the Moloney MuLv vector were combined with 15 mg of lipofectin, a liposome formulation of the cationic lipid N-(1-(2,3-dioleyloxy)propyl)-N, N, N-trimethyl-ammonium chloride and dioleoyl phosphatidyl-ethanolamine, and incubated at room temperature. This mixture was added to the melanoma cell culture, and incubated for 24 h at 37° C. After incubation, cells were washed, and resuspended in fresh culture medium. Forty eight hours later, media was changed and 400 μg/ml of G418 was added for selection of transfectants (A-MM-neu/neo and G-MM-neu/neo). Controls were transfected with pMoNeo only (A-MM-neo and G-MM-neo). Transfection efficiency was $5\times10^{-4}$ to $2\times10^{-4}$.

Transfection was confirmed by flow cytometric assay of cell surface HER2/neu expression in the transfectants. A-MM-neu/neo and G-MM-neu/neo has 76% and 75.9% positive, respectively, and HLA class 1 expression was unaltered (data not shown). Flow cytometric analysis using the anti-HLA-A2 monoclonal antibody BB7.2 revealed that A-MM is HLA-A2 positive and G-MM is HLA-A2 negative.

Six ovarian-specific CTL lines from six different patients were obtained; three of them (CTL 1, 2 and 3) being HLA-A2 positive and CTL 4, 5 and 6 being HLA-A2 negative. CTL 1, 2 and 3 lysed A-MM-neu-neo transfectants (17–20% cytolysis) but neither G-MM-neu-neo transfectants (2–5% cytolysis) nor control transfectants (A-MM-neo and G-MM-neo: 2–5% cytolysis). CTL4 and 6 showed no cytotoxicity (2–5% cytolysis) against any of the transfectants. CTL 5 showed cytoxicity against the A-MM transfectant (15% cytolysis) and its control (15% cytolysis), indicating that this cytotoxicity was not related to HER2/neu expression.

Sensitivity of the A-MM-neu-neo HLA-A2 positive transfectant was inhibited by anti HLA-A2 monoclonal antibody, but not by control antibody (data not shown).

EXAMPLE 4

A Common Antigen System Exists between ovarian and breast cancers.

To determine if a common antigen system might exist between ovarian and breast cancers, we isolated tumor-infiltrating lymphocytes (TIL) from a series of HLA-A2$^+$, HER2/neu$^+$ ovarian (Ov) and breast (Br) cancer specimens. See Example 3. The TIL were cultured with repeated stimulation by irradiated autologous tumor cells until the cultures revealed tumor-specific cytotoxicity when tested against a series of HLA-unmatched allogeneic tumor targets in standard chromium-release assays at am E:T ratio of 20:1, as previously described in Example 3. The tumor-specific CTL lines were typed, and the HLA-A2+ cultures were utilized. HLA-A2 status was confirmed by immunofluorescence staining using BB7.2 and MA2.1 anti-HLA-A2- monoclonal antibodies (ATCC, Rockville, Md.). HLA-A2 negative tumor lines were the gift of the Gynecology Oncology Laboratory at Brigham & Women's Hospital and HLA-A2 negative breast cancer lines were obtained from the ATCC (ATCC #829 and 863). All tumor lines expressed comparable amounts of HER2/neu.

Similarly, the tumors were cultured, and their HER2/neu expression measured by immunofluorescence, and the positives used. HER2/neu expression was determined by immunofluorescence staining with TA-1 anti-HER2/neu monoclonal antibody (Oncogene Science, Uniondale, N.Y.).

Figure 1:
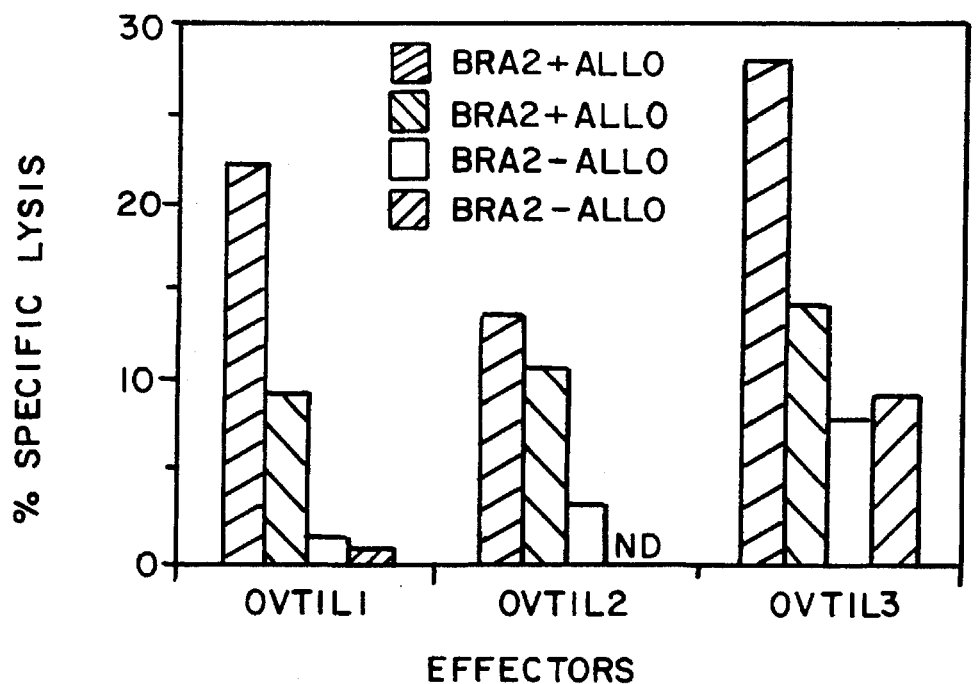
FIG. 1 illustrates results of chromium release assays that demonstrate OvTIL recognition of HLA-A2$^+$, HER2/neu$^+$ breast cancer lines. Three HLA-A2$^+$ ovarian tumor-specific CTL lines were tested against HLA-A2$^+$ and HLA-A2$^-$, HER2/neu$^+$ breast cancer lines in cytotoxicity assays at an E:T ratio of 20:1.
Figure 2:
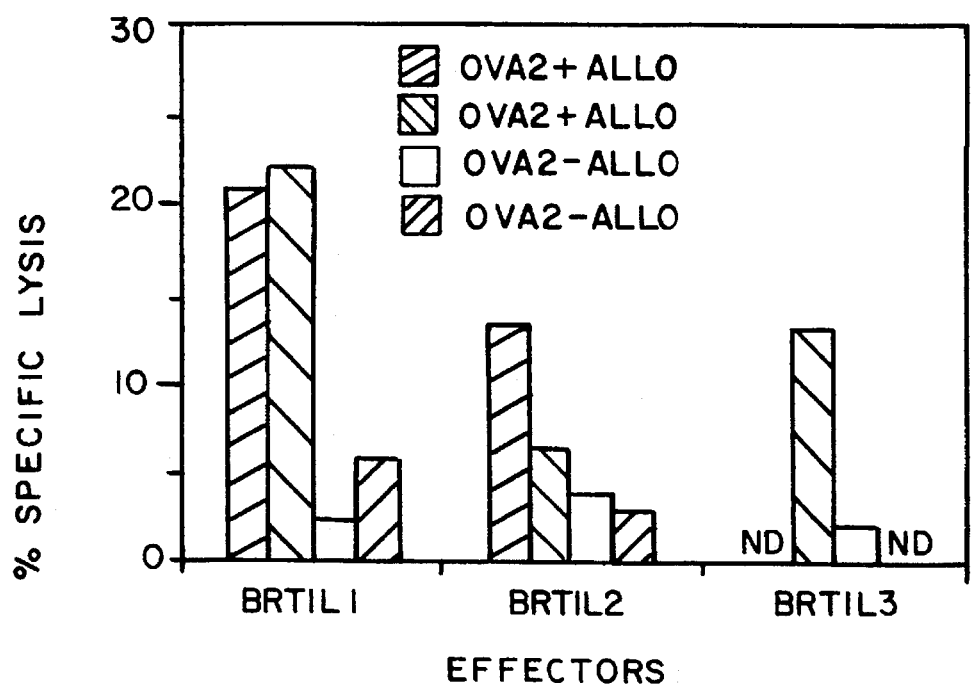
FIG. 2 illustrates results of chromium release assays that demonstrate BrTIL recognition of HLA-A2$^+$, HER2/neu$^+$ ovarian cancer lines. Three HLA-A2$^+$ breast tumor-specific CTL lines were tested against HLA-A2$^+$ and HLA-A2$^-$, HER2/neu$^+$ ovarian cancer lines in cytotoxicity assays at an E:T ratio of 20:1.

The HLA-A2+ OvTIL1, OvTIL2, and OvTIL3 lines recognized and specifically lysed the HLA-A2+ ovarian tumor lines between 2.5–10 times more than the HLA-A2– lines. The HLA-A2+ BrTIL1, BrTIL2, and BrTIL3 lines recognized and lysed HLA-A2+ breast cancer lines at between 2–20 times the lysis of HLA-A2– lines. Interestingly, when these lines were crossed, the OvTIL recognized and lysed the breast cancers and BrTIL recognized and lysed ovarian cancers in similar amounts (FIGS. 1 and 2, respectively).

Neither the OvTIL or the BrTIL recognized HLA-A2+ melanomas, nor did HLA-A2– OvTIL or BrTIL lyse the HLA-A2+ cancer lines. The HER2/neu expression in the HLA-A2+ and HLA-A2– tumors was comparable. This data suggests that HLA-A2 serves as a restriction element in breast cancer also, but more importantly, at least one common tumor antigen system exists between these closely related malignancies and is presented by the HLA-A2 allele.

EXAMPLE 5

Recognition of mutant HER2/neu peptide by cancer-specific lymphocytes.

The T2 cell is a human T cell/B cell fusion product which has an antigen processing defect such that HLA-A2 molecules are present on the cell surface with relatively few endogeous peptides. See Salter et al., Science, 255:1264 (1992). T2 is unique in that it is known to express some empty HLA-A2 molecules but these are only transiently expressed on the cell surface since it is the peptide that stabilizes the HLA molecule. If the temperature is lowered the cell membrane turns over much slower. Therefore, we performed a series of experiments altering the concentration of peptide used, length of loading time, and incubation temperature. The temperature and length of incubation was limited by the viability of the T2 which had already been exposed to an hour of chromium loading. The best loading occurred at 4° C. for 2 hours; however, the cell viability dropped significantly. We currently perform the assays in serum-free media which contains less possible proteins/peptides capable of interfering with the loading of T2. We utilize only the most healthy T2 which has been resuspended for 36 hours prior to the assay and load with 100–200 μg/ml of peptide dissolved in water for 1 hour at 37° C.

Non-small cell lung cancer TIL, OvTIL and BrTIL were tested in standard chromium release assays against the HLA-A2+, antigen-processing cell line, T2, either unloaded or pulsed with SEQ ID NOS.:4 or No.:2 peptide at an E:T ratio of 20:1. After being labelled with chromium, the T2 was incubated with 50–100 ug/ml of either peptide for 1 hr at 37° C. prior to cytotoxicity assays.

Both OvTIL and BrTIL were also tested in standard chromium release assays against T2 pulsed with increasing concentrations of SEQ ID NO.:2 peptide. All incubations were for 1 hr at 37° C., and the E:T ratio was constant at 20:1. Peak recognition occurred at 100 ug/ml. In another experiment, after T2 had been labelled with chromium and pulsed with SEQ ID NO.:2, anti-HLA-A2 mAb, BB7.2 or anti-HLA-A,-B,-C mAb, W6/32 was added at 1:2.

Figure 3:
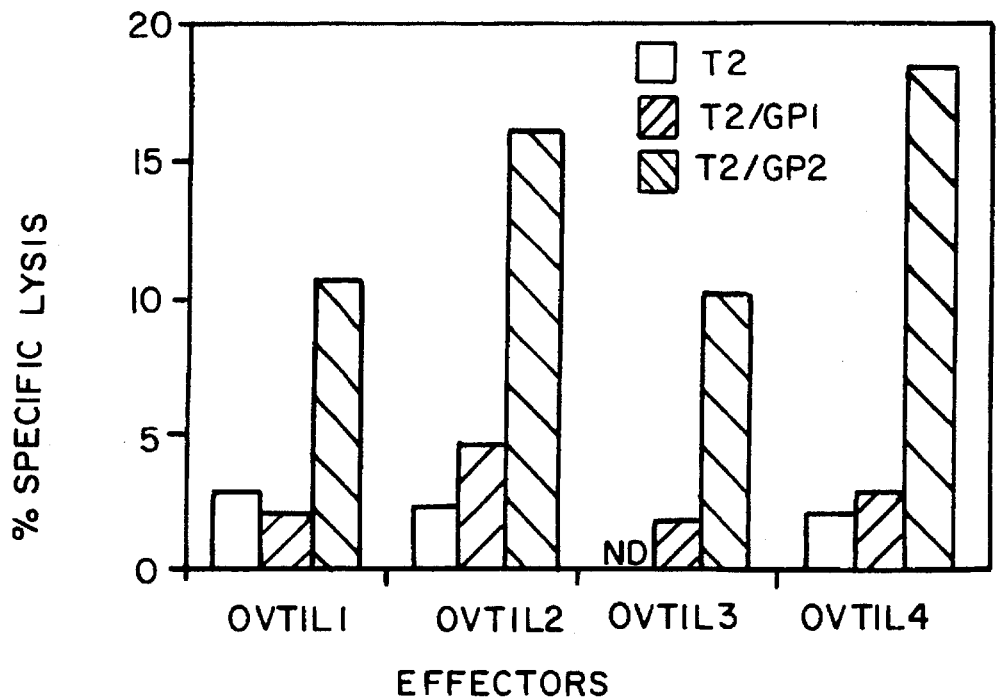
FIG. 3 illustrates results of chromium release assays that demonstrate ovarian tumor-specific CTL's recognize the HER2/neu-derived peptide (SEQ ID NO.:2). OvTIL were tested against T2 either unloaded or pulsed with 50–100 ug of SEQ ID NO.1 or 2 at an E:T ratio of 20:1.

After the T2 cell line was loaded with the synthetic peptides, and four HLA-A2+ ovarian cancer-specific TIL lines recognized the SEQ ID NO.:2 peptide but not the SEQ ID NO.:4 peptide or the unloaded T2 (FIG. 3). The level of recognition of the peptide-pulsed T2 was approximately 50% of that for an HLA-A2+ allogeneic control and was consistent and reproducible in multiple experiments utilizing these CTL lines. The difference in level of lysis may be related to the inefficiency of our current readout system. SEQ ID NO.:2 is extremely hydrophobic as it comes from the transmembrane portion of the protein, and this property made its production and use difficult.

Figure 4:
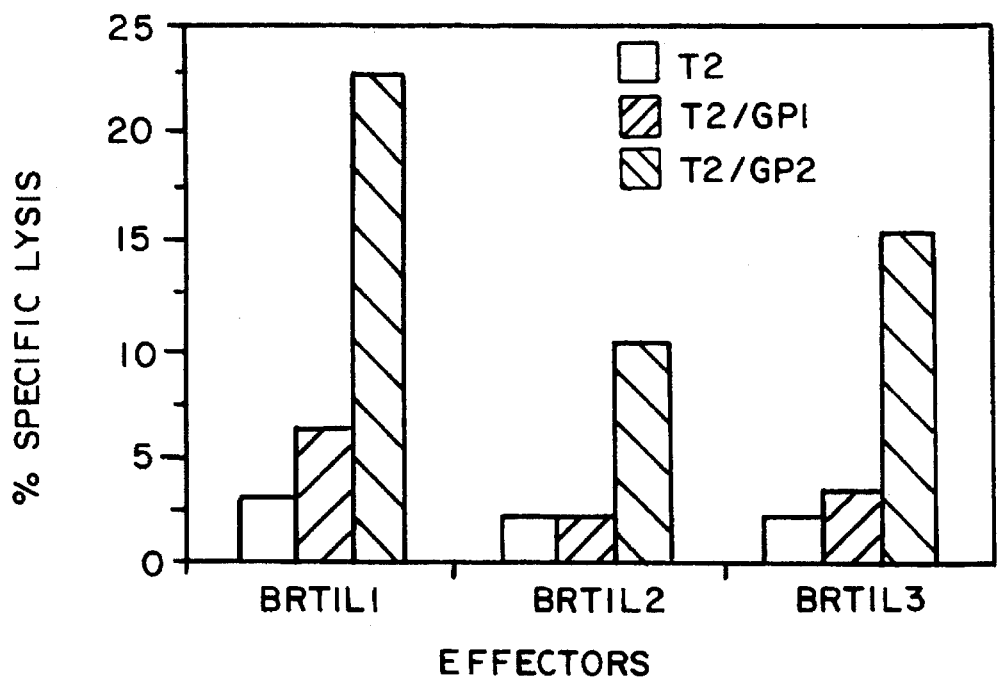
FIG. 4 illustrates results of chromium release assays that demonstrate breast tumor-specific CTL's recognize the HER2/neu-derived peptide (SEQ ID NO.:2). BrTIL were tested against T2 either unloaded or pulsed with 50–100 μg of SEQ ID NO.1 or 2 at an E:T ratio of 20:1.

Of extreme interest, three HLA-A2+ breast cancer-specific TIL lines also recognized SEQ ID NO.:2 peptide but not the SEQ ID NO.:4 peptide or the unloaded T2 (FIG. 4). The level of killing was generally comparable to that found by the OvTIL, and ranged between 10–25% at an effector-:target ratio of 20:1. This range could be related to the effectiveness and overall cytotoxic potential of the effectors utilized, but more likely the degree of recognition is secondary to the level of HER2/neu expression in the autologous tumor with which these lines were stimulated.

An HLA-A2+ lung cancer-specific T-lymphocyte line also recognized SEQ ID NO.:2 ("GP2") but not the SEQ ID NO.:4 peptide ("GP1") or the unloaded T2 (FIG. 7). The level of killing was comparable to that found by OvTIL and BrTIL.

FIG. 5 demonstrates that both OvTIL and BrTIL recognize SEQ ID NO.:2 peptide ("GP2") in a dose-response manner with maximal lysis occurring at approximately 100 ug/ml. No significant recognition of SEQ ID NO.:4 ("GP1") was found at any of these concentrations. The lysis of SEQ ID NO.:2-pulsed T2 was confirmed as being HLA-A2-restricted by monoclonal antibody (mAb) blocking studies. The anti-HLA-A2 mAb, BB7.2 completely inhibited the recognition of SEQ ID NO.:2 by both OvTIL and BrTIL (FIG. 6). The level of BB7.2 blocking was equal to that of the anti-HLA-A-B-C mAb, W6/32, demonstrating that HLA-A2 is the only class I molecule presenting this peptide, as expected. These findings suggest that both ovarian cancer-specific and breast cancer-specific CTL recognize a HER2/neu-derived peptide found only in cancerous cells.

EXAMPLE 6

Generation of CTL Cultures Responsive to HER2/neu Peptide from Peripheral Blood Lymphocytes (PBL)

CTL cultures specific for SEQ ID No.:2 are generated as follows: Briefly, PBL's from HLA-A2+ donors are separated on Hypaque-Ficoll and incubated in RPMI 1640 plus 10% pooled human plasma at $10^6$/ml in the presence of 5 μg/ml antigenic HER2/neu peptide. After 3 days interleukin-2 (Amgen, Thousands Oaks, Calif.) is added (2 U/ml). Seven days later, cells are centrifuged (800×g for 10 min) and resuspended at $5 \times 10^5$ viable cells/ml in the presence of $5 \times 10^5$/ml peptide-pulsed PBL's and 2 U/ml IL-2. Peptide-pulsed PBL's are prepared as follows: About $10^7$ cells are centrifuged and resuspended in 100 μl PBS containing 100 μg HER2/neu peptide. After 1 h at 37° C., the cells are irradiated (2000 R), washed once and added to the cultures. When cell densities exceed $10^6$/ml, cells are diluted to $5 \times 10^5$/ml by centrifugation and resuspended in RPMI 1640 plus 10% pooled human plasma with 2 U/ml IL-2. Every 10 days the cells are pulsed with HER2/neu peptide as described above.

EXAMPLE 7

Construction of Peptide Expression Vector

A. Construction of episomal vector

The expression plasmid p8901 is constructed by ligation of oligonucleotide duplexes containing the Kozak consensus sequence, and coding for the appropriate amino acid residues of the mutant antigenic peptide into the unique BamHI site of plasmid p8901 (Bednarek et al., supra, incorporated herein by reference). Plasmid p8901 contains the following elements 5' to the BamHI cloning site: the SV40 enhancer; the Ad2 ML promoter, and the Ad2 tripartite leader. The 3' flanking sequence following the BamHI insertion site contains the SV40 large T polyadenylation signal. Stable transfection is afforded by the self-replicating EBV episomal replicon that includes both the EBV origin of replication and a functional segment of the EBV nuclear Ag 1 gene. The pBR322 origin of replication (pBRori) and ampicillin-resistance gene (Amp$^r$) allow propagation of the vector in *Escherichia coli*. The *E. coli* hph gene is inserted between the herpes simplex virus thymidine 1 promoter and termination (HSV thymidine 1 promoter) sequences and confers hygromycin B resistance to transfected human cells.

The oligonucleotide duplexes are constructed from synthetic oligonucleotides containing 15 bp of complementary overlap. After extending the annealed pair of oligonucleotides with Klenow and dNTP, polymerase chain reaction is used to amplify the desired duplex. The polymerase chain reaction product (1 μg) is phenol extracted, ethanol precipitated, and digested with BamHI (10 U) and BglII (20 U) for 8 h. The BglII digest generates a cohesive end compatible with BamHI. Ligation of the digested fragment into BamHI digested and alkaline phosphatase-treated p8901 yields the desired expression vector. The orientation of the synthetic inserts is confirmed by sequencing of the double stranded vector using Sequenase (US Biochemicals Corporation, Cleveland, Ohio).

B. Transfection of episomal expression vectors.

Host cells (e.g. T2 cells )($10^7$) are suspended in 0.5 ml RPMI, and 20 μg DNA added. After electroporation at 230 V and 960 μFarad in a Bio-Rad Gene Pulser and Capacitance Extender (Bio-Rad Laboratories, Richmond, Calif.) (0.4 cm electrode gap) cells are incubated on ice for 10 min followed by transfer to 10 ml RPMI/FCS. After 24 h at 37° C. cells are pelleted and resuspended in 24 ml hygromycin B containing medium (150 μg/ml: Sigma Chemical Co., St. Louis, Mo.) and plated at 1 ml/well in 24-well plates.

We have developed three lines of evidence that SEQ ID NO.:2, the mutant antigenic peptide, is actually the endogenous peptide expressed by tumor cells. First, we have performed HPLC on antigenic peptides expressed and presented by cancer cells and have found a reproducible peak that corresponds to that of SEQ ID NO.:2. Second, as shown in the Figures, we have taken synthetic SEQ ID NO.:2 and presented it on empty T2 cells and have exposed it to lymphocytes that have previously been exposed to HLA-A2$^+$ HER2/neu expressing tumors. We have shown that these lymphocytes recognize SEQ ID NO.:2 when presented on T2 cells. Third, with reference to FIG. 8, we have sensitized with SEQ ID NO.:2 "uneducated" ovarian lymphocytes (i.e., that have not yet been stimulated by tumor antigen). These ovarian lymphocytes sensitized with synthetic SEQ ID NO.:2 were challenged with a variety of cells as shown in FIG. 8. Cells included T2 cells presenting SEQ ID NO.:1 and SEQ ID NO.:2; allogeneic HLA-A2+/HER2/neu$^+$ ovarian tumor cells; and allogeneic HLA-A2– ovarian tumor cells.

The results clearly indicate that the sensitized, uneducated ovarian lymphocytes recognize endogenous tumor (bars 3 and 4 of FIG. 8). SEQ ID NO.:2 alone (i.e. when presented on T2 cells) will also induce recognition by the SEQ ID NO.:2-educated lymphocytes (bar 2 of FIG. 8). Thus, since SEQ ID NO.:2-sensitized lymphocytes can recognize endogenous tumor we believe that SEQ ID NO.:2 must be expressed in endogenous tumor and it is capable of being recognized even though it is expressed in small amounts.

Equivalents

It should be understood that the preceding is merely a detailed description of certain preferred embodiments. It therefore should be apparent to those skilled in the art that various modifications and equivalents can be made without departing from the spirit or scope of the invention.

We claim:

1. An isolated peptide consisting of 10 amino acid residues, said isolated peptide having an amine acid sequence consisting of IISAVVGILN, where N is an amine acid selected from the group consisting of L, V, and I.

2. An isolated peptide consisting of 9 amino acids and having the amine acid sequence consisting of IISAVVGIL (SEQ ID NO:2).

* * * * *

UNITED STATES PATENT AND TRADEMARK OFFICE
CERTIFICATE OF CORRECTION

PATENT NO. : 5,550,214
DATED : August 27, 1996
INVENTOR(S) : Timothy J. Eberlein, et. al.

It is certified that error appears in the above-identified patent and that said Letters Patent is hereby corrected as shown below:

Column 8, line 6: please delete "(pro"; and insert therefor -- (Pro --.

Column 13, lines 38 and 39: please delete "4. Introduction into and expression in host cells"; and insert therefor on new line -- 4. Introduction into and expression in host cells --.

Column 13, line 39: please delete "Recombinant vectors containing"; and insert therefor on line 40 -- Recombinant vectors containing --.

Column 17, line 14: please delete "24510"; and insert therefor -- #24510--.

Column 25, line 33: please delete "cpm]X"; and insert therefor -- cmp] --.

Column 26, line 15: please delete "µug"; and insert therefor -- µg --.

Column 35, line 13: please delete "amine"; and insert therefor -- amino --.

Column 35, line 14; please delete "amine"; and insert therefor -- amino --.

Signed and Sealed this

Sixteenth Day of December, 1997

Attest:

*Attesting Officer*

BRUCE LEHMAN
*Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
        Ile  Leu  Ser  Ala  Val  Val  Gly  Ile  Leu
         1              5
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
        Ile  Ile  Ser  Ala  Val  Val  Gly  Ile  Leu
         1              5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
        Xaa  Ile  Xaa  Xaa  Xaa  Val  Xaa  Xaa  Leu
         1              5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
        Pro  Leu  Thr  Ser  Ile  Ile  Ser  Ala  Val
         1              5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
        Tyr  Ile  Ser  Ala  Val  Val  Gly  Ile  Leu
         1              5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
        Phe  Ile  Ser  Ala  Val  Val  Gly  Ile  Leu
         1              5
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATCATCTCTG CGGTGGTTGG CATTCTG           27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATHATHAGYG CNGTNGTNGG NATHTTR           27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATHATHTCHG CNGTNGTNGG NATHTTR           27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATHATHAGYG CNGTNGTNGG NATHCTN           27

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATHATHTGNG CNGTNGTNGG NATHCTN           27

(2) INFORMATION FOR SEQ ID NO:12:

(i) SEQUENCE CHARACTERISTICS:
        (A) LENGTH: 10 amino acids
        (B) TYPE: amino acid -continued (D) TOPOLOGY: linear (ii) MOLECULE TYPE: peptide (xi) SEQUENCE DESCRIPTION: SEQ ID NO:12:

```
Phe  Leu  Pro  Ser  Asp  Tyr  Phe  Pro  Ser  Val
 1              5                        10
```